US 11,884,698 B2

(12) United States Patent
Livigni et al.

(10) Patent No.: US 11,884,698 B2
(45) Date of Patent: Jan. 30, 2024

(54) SYSTEMS AND METHODS FOR PREPARING A POLYPEPTIDE FROM A MIXTURE

(71) Applicant: Regeneron Pharmaceuticals, Inc., Tarrytown, NY (US)

(72) Inventors: Isabelle Livigni, New York, NY (US); Stefanie McDermott, Nyack, NY (US); James Reilly, Putnam Valley, NY (US); John Mattila, Nyack, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 1187 days.

(21) Appl. No.: 16/459,187

(22) Filed: Jul. 1, 2019

(65) Prior Publication Data

US 2020/0002373 A1 Jan. 2, 2020

Related U.S. Application Data

(60) Provisional application No. 62/693,024, filed on Jul. 2, 2018.

(51) Int. Cl.
| | |
|---|---|
| *B01D 15/18* | (2006.01) |
| *B01D 15/30* | (2006.01) |
| *C07K 1/20* | (2006.01) |
| *C07K 1/107* | (2006.01) |
| *C07K 16/06* | (2006.01) |

(52) U.S. Cl.
CPC ........ *C07K 1/1077* (2013.01); *B01D 15/1864* (2013.01); *B01D 15/305* (2013.01); *C07K 1/20* (2013.01); *C07K 16/065* (2013.01)

(58) Field of Classification Search
None
See application file for complete search history.

(56) References Cited

U.S. PATENT DOCUMENTS

| | | |
|---|---|---|
| 4,801,726 A | 1/1989 | Giese et al. |
| 4,937,188 A | 6/1990 | Giese et al. |
| 5,190,864 A | 3/1993 | Giese et al. |
| 5,412,083 A | 5/1995 | Giese et al. |
| 5,641,870 A | 6/1997 | Rinderknecht et al. |
| 6,066,719 A | 5/2000 | Zapata |
| 6,214,984 B1 | 4/2001 | Zapata |
| 6,441,160 B2 | 8/2002 | Kitamura et al. |
| 7,038,017 B2 | 5/2006 | Rinderknecht et al. |
| 7,070,959 B1 | 7/2006 | Papadopoulos et al. |
| 7,101,982 B2 | 9/2006 | Ghose et al. |
| 7,220,356 B2 | 5/2007 | Thommes et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| RE40,070 E | 2/2008 | Shadle et al. |
| 7,374,757 B2 | 5/2008 | Papadopoulos et al. |
| 7,374,758 B2 | 5/2008 | Papadopoulos et al. |
| 7,385,040 B2 | 6/2008 | Johansson et al. |
| 7,393,631 B2 | 7/2008 | Cannon-Carlson et al. |
| 7,427,659 B2 | 9/2008 | Shukla et al. |
| 7,531,173 B2 | 5/2009 | Wiegand et al. |
| 7,608,261 B2 | 10/2009 | Furfine et al. |
| 7,666,413 B2 | 2/2010 | Liu et al. |
| 7,700,097 B2 | 4/2010 | Braslawsky et al. |
| 7,714,112 B2 | 5/2010 | Engstrand et al. |
| 7,750,129 B2 | 7/2010 | Johansson et al. |
| RE41,555 E | 8/2010 | Shadle et al. |
| RE41,595 E | 8/2010 | Shandle et al. |
| 7,795,405 B2 | 9/2010 | DiNovo |
| 7,863,426 B2 | 1/2011 | Wan et al. |
| 7,972,598 B2 | 7/2011 | Daly et al. |
| 8,003,364 B2 | 8/2011 | Post Hansen et al. |
| 8,012,754 B2 | 9/2011 | Rinderknecht et al. |
| 8,029,791 B2 | 10/2011 | Papadopoulos et al. |
| 8,084,032 B2 | 12/2011 | Yumioka et al. |
| 8,092,803 B2 | 1/2012 | Furfine et al. |
| 8,163,531 B2 | 4/2012 | Post Hansen et al. |
| 8,231,876 B2 | 7/2012 | Wan et al. |
| 8,343,349 B2 | 1/2013 | Eriksson et al. |

(Continued)

FOREIGN PATENT DOCUMENTS

| | | | |
|---|---|---|---|
| EP | 2656892 A1 * | 10/2013 | ......... B01D 15/1821 |
| JP | 2009-511900 A | 3/2009 | |

(Continued)

OTHER PUBLICATIONS

"Wolk et al. Improving affinity chromatography resin efficiency using semi-continuous chromatography" J. Chromatography A, 1227 (2012) 154-162 (Year: 2012).*

(Continued)

*Primary Examiner* — Daniel E Kolker
*Assistant Examiner* — James L Rogers
(74) *Attorney, Agent, or Firm* — Bookoff McAndrews, PLLC

(57) ABSTRACT

Embodiments of the present disclosure are directed to methods for preparing a target polypeptide from a mixture including the target polypeptide. The method may include contacting the mixture to a hydrophobic interaction chromatography (HIC) apparatus including multiple chromatographic zones. The method may further include passing the target polypeptide through the outlets of at least a first zone and a second zone of the HIC apparatus. A residence time for the mixture including the target polypeptide in a first zone may be approximately the same as a residence time of one or more mobile phases in the second zone.

11 Claims, 11 Drawing Sheets

(56) References Cited

U.S. PATENT DOCUMENTS

| | | |
|---|---|---|
| 8,343,737 B2 | 1/2013 | Papadopoulos et al. |
| 8,410,928 B2 | 4/2013 | Ganguly et al. |
| 8,435,527 B2 | 5/2013 | Yumioka et al. |
| 8,470,328 B2 | 6/2013 | Yumioka et al. |
| 8,470,578 B2 | 6/2013 | Post Hansen et al. |
| 8,491,904 B2 | 7/2013 | Hickman |
| 8,568,586 B2 | 10/2013 | Cunnien et al. |
| 8,603,473 B2 | 12/2013 | Glaser et al. |
| 8,608,960 B2 | 12/2013 | Thommes et al. |
| 8,647,842 B2 | 2/2014 | Papadopoulos et al. |
| 8,821,865 B2 | 9/2014 | Neu et al. |
| 8,821,879 B2 | 9/2014 | Babuka et al. |
| 8,871,209 B2 | 10/2014 | Stitt et al. |
| 8,895,709 B2 | 11/2014 | Hickman et al. |
| 8,895,710 B2 | 11/2014 | Engstrand et al. |
| 8,946,395 B1 | 2/2015 | Herigstad et al. |
| 8,969,532 B2 | 3/2015 | DeFrees et al. |
| 9,017,687 B1 | 4/2015 | Wang et al. |
| 9,018,361 B2 | 4/2015 | Hickman et al. |
| 9,067,990 B2 | 6/2015 | Wang et al. |
| 9,102,723 B2 | 8/2015 | Wan et al. |
| 9,109,010 B2 | 8/2015 | Hickman et al. |
| 9,109,201 B2 | 8/2015 | Post Hansen et al. |
| 9,150,645 B2 | 10/2015 | Subramanian et al. |
| 9,150,938 B2 | 10/2015 | Oroskar |
| 9,181,572 B2 | 11/2015 | Subramanian et al. |
| 9,193,787 B2 | 11/2015 | Chumsae |
| 9,249,182 B2 | 2/2016 | Herigstad et al. |
| 9,266,950 B2 | 2/2016 | Hickman |
| 9,334,319 B2 | 5/2016 | Ramasubramanyan et al. |
| 9,346,879 B2 | 5/2016 | Ramasubramanyan et al. |
| 9,359,434 B2 | 6/2016 | Subramanian et al. |
| 9,488,625 B2 | 11/2016 | Felgenhauer et al. |
| 9,505,833 B2 | 11/2016 | Chumsae |
| 9,518,082 B2 | 12/2016 | Allison et al. |
| 9,650,411 B2 | 5/2017 | Ishihara |
| 9,650,412 B2 | 5/2017 | Konstantinov et al. |
| 9,650,413 B2 | 5/2017 | Konstantinov et al. |
| 9,657,056 B2 | 5/2017 | Konstantinov et al. |
| 9,683,012 B2 | 6/2017 | Yoon et al. |
| 9,683,033 B2 | 6/2017 | Subramanian et al. |
| 9,688,752 B2 | 6/2017 | Wang et al. |
| 9,708,365 B2 | 7/2017 | Mendiratta et al. |
| 9,708,399 B2 | 7/2017 | Wang et al. |
| 9,708,400 B2 | 7/2017 | Subramanian et al. |
| 9,766,217 B2 | 9/2017 | Kidal et al. |
| 9,878,266 B2 | 1/2018 | Engstrand et al. |
| 9,920,120 B2 | 3/2018 | Yu et al. |
| 9,945,858 B2 | 4/2018 | Gunawan et al. |
| 9,957,318 B2 | 5/2018 | Ramasubramanyan et al. |
| 9,975,948 B2 | 5/2018 | Hickman |
| 9,994,609 B2 | 6/2018 | Ghose et al. |
| 10,017,746 B2 | 7/2018 | Sheldon et al. |
| 10,023,608 B1 | 7/2018 | Ma et al. |
| 10,053,489 B2 | 8/2018 | Kim et al. |
| 10,115,576 B2 | 10/2018 | Geromanos et al. |
| 10,188,732 B2 | 1/2019 | Conley et al. |
| 10,342,876 B2 | 7/2019 | Bak et al. |
| 10,363,496 B2 | 7/2019 | Coutard |
| 10,494,429 B2 | 12/2019 | Yu et al. |
| 10,533,045 B2 | 1/2020 | Allison et al. |
| 10,597,443 B2 | 3/2020 | Schurpf et al. |
| 10,597,446 B2 | 3/2020 | Yu et al. |
| 10,597,447 B2 | 3/2020 | Yu et al. |
| 10,626,376 B2 | 4/2020 | McNally et al. |
| 10,692,709 B2 | 6/2020 | Geromanos et al. |
| 10,696,735 B2 | 6/2020 | Yonan et al. |
| 10,696,952 B2 | 6/2020 | Sheldon et al. |
| 10,702,603 B2 | 7/2020 | Conley et al. |
| 10,788,494 B2 | 9/2020 | Gunawan et al. |
| 10,822,404 B2 | 11/2020 | Yu et al. |
| 10,894,079 B2 | 1/2021 | Mullner et al. |
| 10,940,401 B2 | 3/2021 | Mahajan et al. |
| 10,947,262 B2 | 3/2021 | Gronke et al. |
| 2002/0064860 A1 | 5/2002 | Cannon-Carlson et al. |
| 2004/0106184 A1 | 6/2004 | Senesac |
| 2005/0163782 A1 | 7/2005 | Glaser et al. |
| 2006/0027454 A1 | 2/2006 | DiNovo |
| 2006/0257972 A1 | 11/2006 | Ishihara |
| 2007/0213513 A1 | 9/2007 | Van Alstine et al. |
| 2008/0299545 A1 | 12/2008 | Zhang et al. |
| 2008/0299671 A1 | 12/2008 | Glad et al. |
| 2010/0035299 A1 | 2/2010 | DeFrees et al. |
| 2010/0069617 A1 | 3/2010 | Gagnon |
| 2010/0127860 A1 | 5/2010 | Ganguly et al. |
| 2010/0136025 A1 | 6/2010 | Hickman et al. |
| 2010/0278822 A1 | 11/2010 | Fraunhofer et al. |
| 2011/0147312 A1 | 6/2011 | Cunnien et al. |
| 2012/0122076 A1* | 5/2012 | Lau .................... C07K 1/22 |
| | | 530/416 |
| 2013/0131318 A1 | 5/2013 | Kremer et al. |
| 2013/0149310 A1 | 6/2013 | Jasson et al. |
| 2013/0336957 A1 | 12/2013 | Wang et al. |
| 2014/0010820 A1 | 1/2014 | Wang et al. |
| 2014/0046038 A1 | 2/2014 | Ishihara |
| 2014/0072585 A1 | 3/2014 | Herigstad et al. |
| 2014/0154270 A1 | 6/2014 | Wang et al. |
| 2014/0302053 A1 | 10/2014 | Huang et al. |
| 2014/0356370 A1 | 12/2014 | Swergold et al. |
| 2014/0356371 A1 | 12/2014 | Swergold et al. |
| 2014/0356372 A1 | 12/2014 | Stahl et al. |
| 2015/0170892 A1 | 6/2015 | Geromanos et al. |
| 2015/0210735 A1 | 7/2015 | Hickman et al. |
| 2015/0299249 A1 | 10/2015 | Herigstad et al. |
| 2015/0337029 A1 | 11/2015 | Kyratsous et al. |
| 2016/0083452 A1 | 3/2016 | Hickman et al. |
| 2016/0101181 A1 | 4/2016 | Bak et al. |
| 2016/0115193 A1 | 4/2016 | Herigstad et al. |
| 2016/0152717 A1 | 6/2016 | Cao et al. |
| 2016/0215040 A1 | 7/2016 | Kyratsous et al. |
| 2016/0251441 A1 | 9/2016 | O'Connor et al. |
| 2016/0320391 A1 | 11/2016 | Gunawan et al. |
| 2017/0101472 A1 | 4/2017 | Ullman et al. |
| 2017/0158760 A1 | 6/2017 | Hickman et al. |
| 2017/0174779 A1 | 6/2017 | Varghese et al. |
| 2017/0174781 A1 | 6/2017 | Brownstein |
| 2017/0342145 A1 | 11/2017 | Wang et al. |
| 2017/0349654 A1 | 12/2017 | Wang et al. |
| 2018/0222938 A1 | 8/2018 | Herigstad et al. |
| 2018/0230210 A1 | 8/2018 | Hickman |
| 2019/0062419 A1 | 2/2019 | Ramasubramanyan et al. |
| 2019/0144495 A1 | 5/2019 | Ghose et al. |
| 2019/0248823 A1 | 8/2019 | Gronke et al. |
| 2019/0263855 A1* | 8/2019 | Gadgil .................... C07K 1/22 |
| 2019/0298829 A1 | 10/2019 | Wan et al. |
| 2020/0223913 A1 | 7/2020 | Allison et al. |
| 2021/0009632 A1 | 1/2021 | Tan et al. |
| 2021/0010055 A1 | 1/2021 | Cura et al. |

FOREIGN PATENT DOCUMENTS

| | | | |
|---|---|---|---|
| JP | 2010-530068 A | 9/2010 | |
| JP | 2015-520667 A | 7/2015 | |
| KR | 20180064316 A | 6/2018 | |
| WO | 9625425 A1 | 8/1996 | |
| WO | 2007110339 A1 | 10/2007 | |
| WO | WO-2008153472 A1 * | 12/2008 | ......... B01D 15/1828 |
| WO | 2009058769 A1 | 5/2009 | |
| WO | 2010019814 A1 | 2/2010 | |
| WO | 2011028961 A2 | 3/2011 | |
| WO | 2011098526 A1 | 8/2011 | |
| WO | 2012/030512 A1 | 3/2012 | |
| WO | 2012065072 A2 | 5/2012 | |
| WO | 2013066707 A1 | 5/2013 | |
| WO | 2013078170 A1 | 5/2013 | |
| WO | 2013176754 A1 | 11/2013 | |
| WO | 2013177115 A2 | 11/2013 | |
| WO | 2013177118 A2 | 11/2013 | |
| WO | 2014100143 A2 | 6/2014 | |
| WO | 2014143185 A1 | 9/2014 | |
| WO | 2014158231 A1 | 10/2014 | |
| WO | 2015035180 A1 | 3/2015 | |
| WO | 2015038888 A1 | 3/2015 | |
| WO | 2017/140881 A1 | 8/2017 | |

(56) References Cited

FOREIGN PATENT DOCUMENTS

| | | |
|---|---|---|
| WO | 2018027195 A1 | 2/2018 |
| WO | 2019040671 A1 | 2/2019 |
| WO | 2019178495 A1 | 9/2019 |
| WO | 2019246153 A1 | 12/2019 |
| WO | 2020023566 A1 | 1/2020 |
| WO | 2020037016 A1 | 2/2020 |
| WO | 2020096958 A1 | 5/2020 |
| WO | 2020172658 A1 | 8/2020 |
| WO | 2020205469 A1 | 10/2020 |
| WO | 2020264411 A1 | 12/2020 |

OTHER PUBLICATIONS

GE Healthcare Bio-Sciences AB, "Instructions 28995533 AC Hydrophobic interaction resin," 2008.

Godawat, R. et al., "Periodic counter-current chromatography—design and operational considerations for integrated and continuous purification of proteins," Biotechnol. J., 7, 1496-1508, 2012.

Ichihara, T. et al., "Integrated flow-through purification for therapeutic monoclonal antibodies processing," mAbs, Jan. 16, 2018.

International Search Report in PCT/US2019/040148, dated Sep. 23, 2019 (3 pages).

Holzer et al., "Multicolumn Chromatography A New Approach to Relieving Capacity Bottlenecks for Downstream Processing Efficiency", BioProcess International, Sep. 1, 2008, pp. 74-81, XP055614994.

\* cited by examiner

SYSTEMS AND METHODS FOR PREPARING A POLYPEPTIDE FROM A MIXTURE

CROSS-REFERENCE TO RELATED APPLICATIONS

This application claims priority to U.S. Provisional Application No. 62/693,024, filed Jul. 2, 2018, which is incorporated by reference herein in its entirety.

TECHNICAL FIELD

This disclosure generally relates to methods for preparing a polypeptide. More specifically, this disclosure relates to methods for preparing a polypeptide from a mixture using a chromatographic method.

BACKGROUND

Chromatography, such as hydrophobic interaction chromatography (HIC), affinity chromatography, and the like, may be performed as a part of drug product preparation processes. In some instances, chromatography may be particularly useful in the preparation of drug products including polypeptides. However, the equipment, materials, preparation time, and running time for standard batch HIC steps or other batched chromatography steps may result in added costs or reduced efficiency in drug product preparation processes. Specifically, the time needed to run each stage in a HIC or other chromatography separation process, the amount of buffer and/or separation medium used, and any non-automated aspects of the process may reduce the efficiency of drug product preparation.

The methods and systems disclosed herein may improve the efficiency and/or productivity of polypeptide preparation methods. Methods and systems disclosed herein may also improve the efficiency and/or productivity of drug product preparation methods and may address one or more problems identified above.

SUMMARY

Embodiments of the present disclosure may be directed to a method for preparing a target polypeptide from a mixture including the target polypeptide. The method may include contacting the mixture including the target polypeptide to a first zone of a HIC apparatus, contacting mobile phases to a second zone of the HIC apparatus, and passing the target polypeptide through the outlets of the first and second zones of the HIC apparatus, where each of the first zone and the second zone may have one or more chromatographic columns and an outlet. In some embodiments, a residence time for the mixture including the target polypeptide in the first zone may be configured to be approximately the same as a residence time of the mobile phases in the second zone.

In some embodiments, the target polypeptide may be a monoclonal antibody. The target polypeptide may be prepared at a productivity greater than or equal to 50 g/L·hr. Alternatively, or in addition, the mobile phases may include an equilibration buffer and a wash buffer. In some embodiments, methods of the present disclosure may further include passing an effluent including the target polypeptide from the first zone of the HIC apparatus to the second zone of the HIC apparatus. In some embodiments, contacting the mobile phases to the second zone of the HIC apparatus may include contacting a wash buffer to the second one of the HIC apparatus, and after contacting the wash buffer to the second zone of the HIC apparatus, regenerating the second zone. In some embodiments, regenerating the second zone may include contacting water to the second zone of the HIC apparatus, contacting an alkaline solution to the second zone of the HIC apparatus, contacting an alcohol solution to the second zone of the HIC apparatus, and contacting an equilibration buffer to the second zone of the HIC apparatus. The target polypeptide may be passed through the outlet of the second zone of the HIC apparatus after a wash buffer is contacted to the second zone of the HIC apparatus. In some embodiments, one or more of an ultraviolet absorption, electrical conductivity, or pH of a resident solution may be measured at the outlet of either the first zone or the second zone. The first zone or the second zone may include more than one chromatographic column. In some embodiments, the HIC apparatus may further include a third zone having a chromatographic column and an outlet. In some embodiments, the method may further include performing a regeneration cycle on the third zone, wherein performing the regeneration cycle includes contacting mobile phases to the third zone, where a duration for the regeneration cycle is configured to be approximately the same as the residence time for the mixture including the target polypeptide in the first zone.

In some embodiments of the present disclosure, a method for preparing a target polypeptide from a mixture including the target polypeptide may include passing the mixture including the target polypeptide to a first column of a plurality of chromatographic columns in a HIC apparatus, passing an effluent including the target polypeptide from the first column to a second column of the plurality of columns, passing one or more mobile phases to a third column of a plurality of columns, and passing the target polypeptide through the outlets of each of the plurality of columns, where each of the plurality of columns includes an outlet connectable to another column of the plurality of columns and a sum of residence times for the mixture including the target polypeptide in the first column and second column is substantially the same as the sum of the residence times of the one or more mobile phases in the third column.

In some embodiments, the method may further include passing one or more mobile phases to each of the plurality of columns. In some embodiments, passing one or more mobile phases to a column may include passing a wash buffer to the column, and after passing a wash buffer to the column, regenerating the column, where regenerating the column includes passing water, an alkaline solution, an alcohol solution, or an equilibration buffer to the column. In some embodiments, the step of passing a target polypeptide through the outlet of a column may occur after a wash buffer has been passed to the column. In some embodiments, one or more of an ultraviolet absorption, electrical conductivity, or pH of a resident solution are measured at the outlet of either the first column or second column. In some embodiments, the method may include preparing the target polypeptide at a productivity greater than or equal to 50 g/L·hr. In further embodiments, the HIC apparatus may include four columns and the sum of the residence times for the mixture including the target polypeptide in the first column and the second column may be substantially the same as the sum of the regeneration times of the third column and the fourth column.

Further embodiments of the present disclosure may include a method for preparing an antibody using a plurality of chromatographic columns wherein each of the plurality of chromatographic columns includes a hydrophobic interaction medium. The method may include, in a first stage, loading a quantity of a mixture including the antibody into a first column of the plurality of columns, loading a quantity of the mixture into a second column of the plurality of columns via the first column, and performing a non-loading step including at least one of washing, stripping, and equilibration processes in a third column of the plurality of columns; in a second stage, loading a quantity of the mixture including the antibody into the second column, loading a quantity of the mixture into the third column via the second column, and performing the non-loading step including at least one of washing, stripping, and equilibration processes in the first column; and in a third stage, loading a quantity of the mixture including the antibody into the third column, loading a quantity of the mixture into the third column via the second column, and performing the non-loading step including at least one of washing, stripping, and equilibration processes in the second column.

In some embodiments, the method may further include continuously repeating the first, second, and third stages in a cycle, wherein each stage includes performing the loading and non-loading steps simultaneously. In some embodiments, a duration of one of the loading steps is configured to be approximately the same as a duration of the non-loading step.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments. Any features of an embodiment or example described herein (e.g., composition, formulation, method, etc.) may be combined with any other embodiment or example, and all such combinations are encompassed by the present disclosure. Moreover, the described systems and methods are neither limited to any single aspect nor embodiment thereof, nor to any combinations or permutations of such aspects and embodiments. For the sake of brevity, certain permutations and combinations are not discussed and/or illustrated separately herein.

Figure 1:
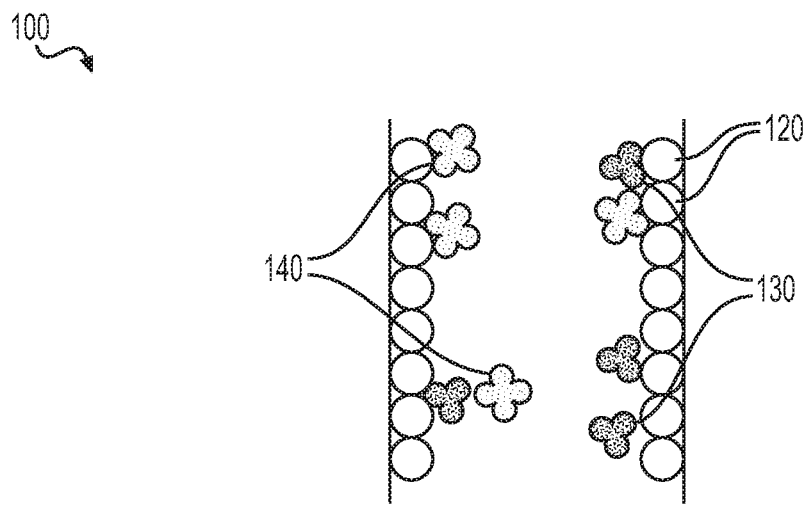
FIG. 1 is a schematic illustration depicting part of a zone of a chromatography apparatus, according to some embodiments of the present disclosure.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." For the terms "for example" and "such as," and grammatical equivalences thereof, the phrase "and without limitation" is understood to follow unless explicitly stated otherwise.

As used herein, the term "about" is meant to account for variations due to experimental error. When applied to numeric values, the term "about" may indicate a variation of +/−10% (unless a different variation is specified) from the disclosed numeric value. As used herein, the singular forms "a," "an," and "the" include plural referents unless the context clearly dictates otherwise.

It should be noted that all numeric values disclosed herein (including all disclosed values, limits, and ranges) may have a variation of +/−10% (unless a different variation is specified) from the disclosed numeric value. Moreover, in the claims, values, limits, and/or ranges means the value, limit, and/or range+/−10%. Similarly, the phrase "approximately the same", as used herein, may mean equivalent within a variation of +/−10%. Further, all ranges are understood to be inclusive of endpoints, e.g., from 1 centimeter (cm) to 5 cm would include lengths of 1 cm, 5 cm, and all distances between 1 cm and 5 cm.

DETAILED DESCRIPTION

This disclosure is not limited to the particular compositions, formulations, material manufacturer, drug products, devices, systems, experimental conditions, or specific methods disclosed herein, as many variations are possible within the purview of one of ordinary skill in the art. The terminology used herein is for the purpose of describing particular embodiments only, and is not intended to be limiting.

Unless defined otherwise, all technical and scientific terms used herein have the same meaning as is commonly understood by one of ordinary skill in the art to which this disclosure belongs. Although any methods and materials similar or equivalent to those described herein can be used in the practice or testing of the present disclosure, particular methods and are now described. All publications mentioned are hereby incorporated by reference.

The term "contacting" as used herein refers to the meeting, joinder, interface, or other physical interaction of two or more surfaces, solutions, or compounds. Although specific fluids may be described herein as being passed into a region, passed from a region, passed to a region, or passed through a region, it is understood that the fluid would necessarily contact any region to which it is passed into, from, to, or through. Similarly, introducing a fluid or component to a region would constitute the fluid or component contacting the region.

The term "polypeptide" as used herein refers to any amino acid polymer having more than about 20 amino acids covalently linked via amide bonds. Proteins contain one or more amino acid polymer chains (e.g., polypeptides). Thus, a polypeptide may be a protein, and a protein may contain multiple polypeptides to form a single functioning biomolecule.

Post translational modifications may further modify or alter the structure of a polypeptide. For example, disulfide bridges (e.g., S—S bonds between cysteine residues) may be present in some proteins. Some disulfide bridges are essential to proper structure, function, and interaction of polypeptides, immunoglobulins, proteins, co-factors, substrates, and the like. In addition to disulfide bond formation, proteins may be subject to other post-translational modifications. Those modifications include lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). Post-translational modifications may affect the hydrophobicity, electrostatic surface properties, or other properties which determine the surface-to-surface interactions participated in by the polypeptide.

As used herein, the term "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, antibody-like molecules, nanobodies, recombinant antibody chimeras, cytokines, chemokines, peptide hormones, and the like. A protein-of-interest (POI) may include any polypeptide or protein that is desired to be isolated, purified, or otherwise prepared. POIs may include target polypeptides or other polypeptides produced by a cell, including antibodies.

The term "antibody," as used herein, includes immunoglobulins comprised of four polypeptide chains: two heavy (H) chains and two light (L) chains inter-connected by disulfide bonds. Typically, antibodies have a molecular weight of over 100 kDa, such as between 130 kDa and 200 kDa, such as about 140 kDa, 145 kDa, 150 kDa, 155 kDa, or 160 kDa. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

A class of immunoglobulins called Immunoglobulin G (IgG), for example, is common in human serum and comprises four polypeptide chains—two light chains and two heavy chains. Each light chain is linked to one heavy chain via a cystine disulfide bond, and the two heavy chains are bound to each other via two cystine disulfide bonds. Other classes of human immunoglobulins include IgA, IgM, IgD, and IgE. In the case of IgG, four subclasses exist: IgG 1, IgG 2, IgG 3, and IgG 4. Each subclass differs in their constant regions, and as a result, may have different effector functions. In some embodiments described herein, a POI may comprise a target polypeptide including IgG. In at least one embodiment, the target polypeptide comprises IgG 4.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Target polypeptides may be produced using recombinant cell-based production systems, such as the insect bacculovirus system, yeast systems (e.g., *Pichia* sp.), mammalian systems (e.g., CHO cells and CHO derivatives like CHO-K1 cells). The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, bacculovirus-infected insect cells, Trichoplusiani, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell). A protein or polypeptide other than the target polypeptide or POIs produced by the cell may be referred to as a host-cell protein (HCP). When a POI is manufactured in and/or purified from host cells, HCPs may be characterized as product- and process-related contaminants or impurities.

Some HCPs (e.g., enzymes) may copurify with POIs (e.g., target polypeptides) and may affect components of the mixtures, formulations, or drug products including the POIs.

For example, the presence of some HCPs may affect product stability, reduce a drug product's shelf life, or even result in the product's failure to meet compendial or regulatory particulate matter specifications (e.g., U.S. Food & Drug Administration specifications). As a further example, some HCPs may cause clinical effects, such as an immunogenic reaction upon administration. While HIC or other chromatography, alone or in combination, may be used to purify and/or separate a POI and remove HCPs from a mixture, formulation, or drug product, thus reducing potential effects of HCPs on a drug product, the addition of a HIC or affinity chromatography step requires adding equipment, materials (e.g., hydrophobic interaction media), and preparation. This equates to added time, resources, experimentation, and costs. Therefore, it is desirable to have an efficient method of conducting a chromatography process to separate a POI (e.g., target polypeptide) from one or more copurified HCPs or other impurities.

The term "chromatography," as used herein, refers to any process which separates components of a mixture by passing the mixture through a medium such that the components of the mixture pass through the medium at different rates, including, but not limited to, column chromatography, planar chromatography, thin layer chromatography, displacement chromatography, gas chromatography, affinity chromatography, ion-exchange chromatography, size-exclusion chromatography, reverse phase chromatography, hydrophobic interaction chromatography (HIC), fast protein liquid chromatography, high-performance liquid chromatography, countercurrent chromatography, periodic counter-current chromatography, or chiral chromatography. While embodiments herein may be disclosed with respect to an exemplary type of chromatography process (e.g., HIC) or apparatus, embodiments disclosed herein may be applicable to any type of chromatography.

As used herein, the term "water" may refer to any suitable type of laboratory grade water, such as deionized water or water for injection. In some embodiments, for example, chromatography apparatuses may be contacted with either deionized water or water for injection. Any reference to the use of "water" herein may refer to deionized water, water for injection, or another type of laboratory grade water.

As used in the present disclosure, the term "mobile phase" may refer to any fluid suitable for contacting a chromatography zone or column as a part of a separation or purification process. A mobile phase may include, for example, water, a buffer solution, an acidic solution, an alkaline solution, and/or a solution comprising alcohol. The terms "wash buffer," "stripping buffer," and "equilibration buffer" may be used to describe mobile phases having particular characteristics, as described further herein.

In some embodiments, a method for preparing a target polypeptide from a mixture including the target polypeptide may comprise contacting the mixture to a chromatography apparatus. The chromatography apparatus may comprise a plurality of zones where each zone includes one or more chromatographic columns where the one or more chromatographic columns comprise hydrophobic interaction media. Such chromatography apparatuses may include pre-manufactured apparatuses (e.g., Cadence™ BioSMB (Pall Biosciences), BioSC® (novasep), Varicol® (novasep), or Octave (Semba® Biosciences)), hand-assembled apparatuses, or merely two or more standard batch chromatography apparatuses used in tandem.

Aspects of the present disclosure may provide various benefits to the process of preparing a target polypeptide or other molecule. For example, simultaneous use of multiple zones in a chromatography apparatus may allow for more efficient and fuller loading of individual columns, and/or the performance of separation processes with the use of less chromatographic media than in a standard chromatography process. Additional benefits and advantages of aspects of the present disclosure will be apparent to those of ordinary skill in the art.

Reference will now be made to the drawings of the present disclosure.

FIG. 1 depicts a section 100 of a chromatographic column of a HIC apparatus, according to some embodiments of the present disclosure. The chromatographic column comprises hydrophobic interaction media. The hydrophobic interaction media comprises a support structure 110 and a hydrophobic moiety 120, wherein the hydrophobic moiety 120 is affixed to the support structure 110. The media can be in the form of chromatography media, e.g., beads or other particles held in a packed bed column format, in the form of a membrane, or in any format that can accommodate a mixture or other liquid comprising a target polypeptide (or other POI) and contaminants (e.g., HCPs). Thus, example hydrophobic interaction media may include agarose beads (e.g., sepharose), silica beads, cellulosic membranes, cellulosic beads, hydrophilic polymer beads, and the like.

A chromatographic column of a HIC apparatus of the present disclosure may be configured such that the hydrophobic interaction medium has a depth (e.g., bed height) of about 0.5 centimeters (cm) to about 40 cm. In some embodiments, for example, the chromatographic column of a HIC apparatus may have a bed height of about 0.5 cm to about 30 cm, of about 0.5 cm to about 20 cm, of about 0.5 cm to about 10 cm, of about 0.5 cm to about 5 cm, of about 1 cm to 20 cm, of about 1 cm to about 10 cm, or of about 1 cm to about 5 cm. In some embodiments, a chromatographic column may be configured such that the inner diameter of the chromatographic column is about 0.5 cm to about 150 cm. In some embodiments, for example, the inner diameter of the chromatographic column is about 0.5 cm to about 140 cm, about 0.5 cm to about 120 cm, about 0.5 cm to about 100 cm, about 0.5 cm to about 80 cm, about 0.5 cm to about 60 cm, about 0.5 cm to about 40 cm, about 0.5 cm to about 20 cm, about 0.5 cm to about 10 cm, about 0.75 cm to about 8 cm, about 1 cm to about 6 cm, about 1 cm to about 5 cm, about 1 cm to about 3 cm, about 1.5 cm to about 5 cm, about 1.5 cm to about 3 cm, or about 1 cm to about 2 cm. For example, in some embodiments, the inner diameter of the chromatographic column is about 0.5 cm, about 1 cm, about 5 cm, about 8 cm, about 10 cm, about 15 cm, about 20 cm, about 30 cm, about 40 cm, about 50 cm, about 60 cm, about 80 cm, about 100 cm, about 125 cm, or about 150 cm. In some embodiments, a chromatographic column of a HIC apparatus according to the present disclosure has a total volume (e.g., total capacity for holding a mixture, mobile phase, or other substance) of about 0.4 milliliters (mL) to about 175 L. In some embodiments, for example, a chromatographic column of a HIC apparatus according to the present disclosure has a total volume of about 0.5 mL to about 150 L, of about 0.5 mL to about 130 L, of about 0.5 mL to about 115 L, of about 0.5 mL to about 100 L, of about 0.5 mL to about 80 L, of about 0.5 mL to about 60 L, of about 0.5 mL to about 40 L, of about 0.5 mL to about 20 L, of about 0.5 mL to about 15 L, of about 0.5 mL to about 10 L, of about 0.5 mL to about 5 L, of about 0.5 mL to about 1 L, of about 1 mL to about 750 mL, of about 1 mL to about 600 mL, of about 1 mL to about 500 mL, of about 1 mL to about 300 mL, of about 1 mL to about 250 mL, of about 1 mL to about 200 mL, or of about 1 mL to about 150 mL. For example, in some embodiments, a chromatographic column according to the present disclosure may have a total volume of about 0.5 mL, about 1 mL, about 5 mL, about 10 mL, about 50 mL, about 100 mL, about 150 mL, about 300 mL, about 400 mL, about 500 mL, about 1 L, about 5 L, about 10 L, about 50 L, about 80 L, about 100 L, about 120 L, or about 150 L.

In some embodiments, the hydrophobic moiety 120 binds to hydrophobic regions and hydrophobic surfaces of polypeptides. The hydrophobic surfaces may be part of the structure of the amino acids composing the peptides, an aforementioned or other post-translational modification, or a combination thereof. The degree of hydrophobicity of the hydrophobic interaction media may be controlled by selecting an appropriate hydrophobic moiety 120. Hydrophobic moiety 120 may be selected to bind to a particular target polypeptide or POI, and may be any now-known or future-developed hydrophobic moiety. In some embodiments hydrophobic moiety 120 may include a methyl, propyl, isopropyl, butyl, hexyl, octyl, and/or phenyl group. Those skilled in the art will appreciate the hydrophobicity of the selected hydrophobic moiety 120 may vary based on target polypeptides and/or HCPs/other impurities of the given application, as well as the type and degree of separation or purification desired from the chromatography process.

The hydrophobic interaction media may be employed to separate target polypeptides or other POIs from product and process related contaminants and impurities (e.g., HCPs). Still referring to FIG. 1, in some embodiments, a mixture containing target polypeptide 140 and other components, such as contaminants 130 (e.g., impurities, HCPs, or the like) are loaded into a HIC apparatus. The mixture may include a solution (e.g., a buffer) designed to promote binding of hydrophobic groups in the target polypeptide 140 to the hydrophobic moiety 120 of the hydrophobic interaction media. Some target polypeptide 140 adheres to the media by binding via intramolecular force to the hydrophobic moiety 120 while other target polypeptide 140 may pass through the chromatographic column. Additionally or alternatively, while the mixture passes through a column, some contaminants 130 from the mixture may adhere to the hydrophobic interaction media by binding via intramolecular force to the hydrophobic moiety 120 while other contaminants 130 fail to bind to the hydrophobic moiety 120. In some embodiments, the target polypeptide 140 contains certain hydrophobic regions from the constituent amino acids, post-translational modifications, or combination thereof that allow it to affix to the hydrophobic moiety 120 with a higher affinity than certain contaminants or impurities (e.g., HCPs). As described in greater detail later, additional mobile phases may then be introduced into the column to lower the affinity between the target polypeptide 140 and the hydrophobic moiety 120, allowing the target polypeptide 140 to pass through the chromatographic column of the HIC apparatus.

In further embodiments, contaminants 130 may affix to the hydrophobic moiety 120 with a higher affinity than the target polypeptide 140. Additional mobile phases may then be introduced into the column to lower the affinity between the contaminants 130 and the hydrophobic moiety 120, allowing the contaminants 130 to pass through the chromatographic column of the HIC apparatus.

The composition of the mixture including the target polypeptide 140 may be altered by the addition of an additive including a salt such as, for example, sodium, potassium, phosphate, tris(hydroxmethyl)aminomethane (Tris), citrate, or acetate. Other additives may be added to alter the hydrophobic or other intramolecular interactions of the target polypeptide 140, Contaminants 130, hydrophobic moiety 120, or combinations thereof.

Figure 2:
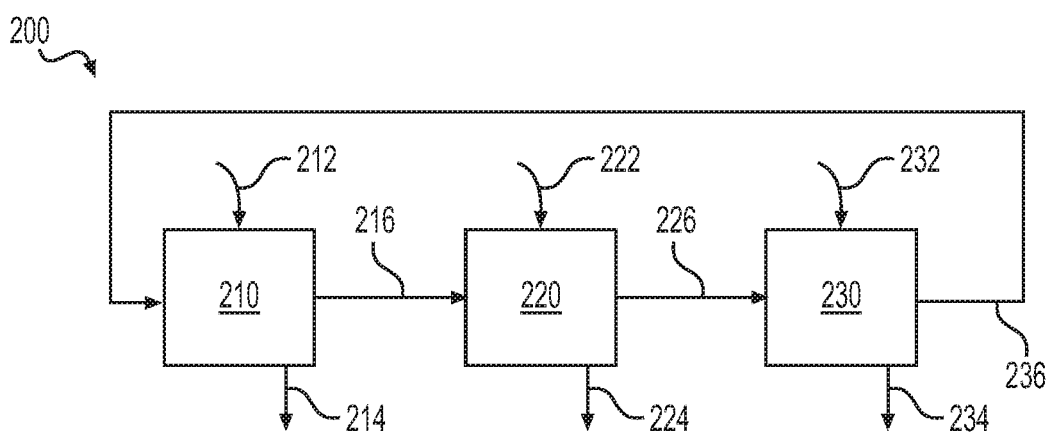
FIG. 2 is a schematic depiction of a chromatography apparatus, according to some embodiments of the present disclosure.

An exemplary HIC apparatus 200 is schematically depicted in FIG. 2, according to some embodiments described herein. The HIC apparatus 200 may comprise a first zone 210, a second zone 220, and a third zone 230. Each of the first zone 210, second zone 220, and third zone 230 may include one or more chromatographic columns, such as the chromatographic columns described with respect to FIG. 1. The first zone 210 may have a first inlet 212 configured such that a mixture including a target polypeptide, one or more mobile phases, or other liquids may be passed to the first zone 210. The first zone 210 may also have a first outlet 214 through which effluent (e.g., fluid which has passed through the first zone 210) may be passed from the HIC apparatus 200 to be collected or discarded. Effluent may also be passed from the first zone 210 to the second zone 220 via a first interconnect 216. The first zone 210 may also receive effluent from the third zone 230 via a third interconnect 236.

The second zone 220 may receive effluent from the first zone 210 via first interconnect 216. The second zone 220 may also have a second inlet 222 configured such that a mixture including a target polypeptide, one or more mobile phases, or other liquids may be passed to the second zone 220. The second zone 220 may also have a second outlet 224 through which effluent (e.g., fluid which has passed through the second zone 220) may be passed from the HIC apparatus 200 to be collected or discarded. Effluent may also be passed from the second zone 220 to the third zone 230 via a second interconnect 226.

The third zone 230 may receive effluent from the second zone 220 via second interconnect 226. The third zone 230 may have a third inlet 232 configured such that a mixture including a target polypeptide, one or more mobile phases, or other liquids may be passed to the third zone 230. The third zone 230 may also have an outlet 234 through which effluent (e.g., fluid which has passed through the third zone 230) may be passed from the HIC apparatus 200 to be collected or discarded. Effluent may also be passed from the third zone 230 to the first zone 220 via a third interconnect 236.

As those of skill in the art would understand, various components known to be used in chromatographic apparatuses (e.g., filters, sensors, gauges, thermometers) may be incorporated into HIC apparatus 200, though not shown in the simplified schematic of FIG. 2. In some embodiments, one or more of a UV absorption, electrical conductivity, or pH or a resident solution may be measured at one or more points in the HIC apparatus 200. Suitable points for measuring UV absorption, electrical conductivity, or pH include at an inlet 212, 222, 232, within a zone 210, 220, 230, at an interconnect 216, 226, 236, or at an outlet 214, 224, 234. Inlets 212, 222, 232, interconnects 216, 226, 236, and outlets 214, 224, 234 may be operable to move from an open configuration to a closed configuration: an open configuration allowing a fluid to pass through the inlet 212, 222, 232, interconnect 216, 226, 236, or outlet 214, 224, 234 and a closed configuration preventing a fluid from passing through the inlet 212, 222, 232, interconnect 216, 226, 236, or outlet 214, 224, 234. A HIC apparatus 200 may include one or more pumps that provide pressure to transmit fluid between zones 210, 220, 230, inlets 212, 222, 232, interconnects 216, 226, 236, and outlets 214, 224, 234. In some embodiments, one or more interconnects 216, 226, 236 may be moved to join different zones 210, 220, 230. For example, during a process using HIC apparatus 200 it may be desirable to rearrange where interconnect 226 passes effluent from zone 220. In those situations, interconnect 226 may be reconfigured, without interrupting the chromatographic process, to pass effluent from zone 220 to zone 210. This is just one example; in general, any interconnect 216, 226, 236 may be reconfigured to connect different zones without interrupting an ongoing chromatographic process.

Figure 3A:
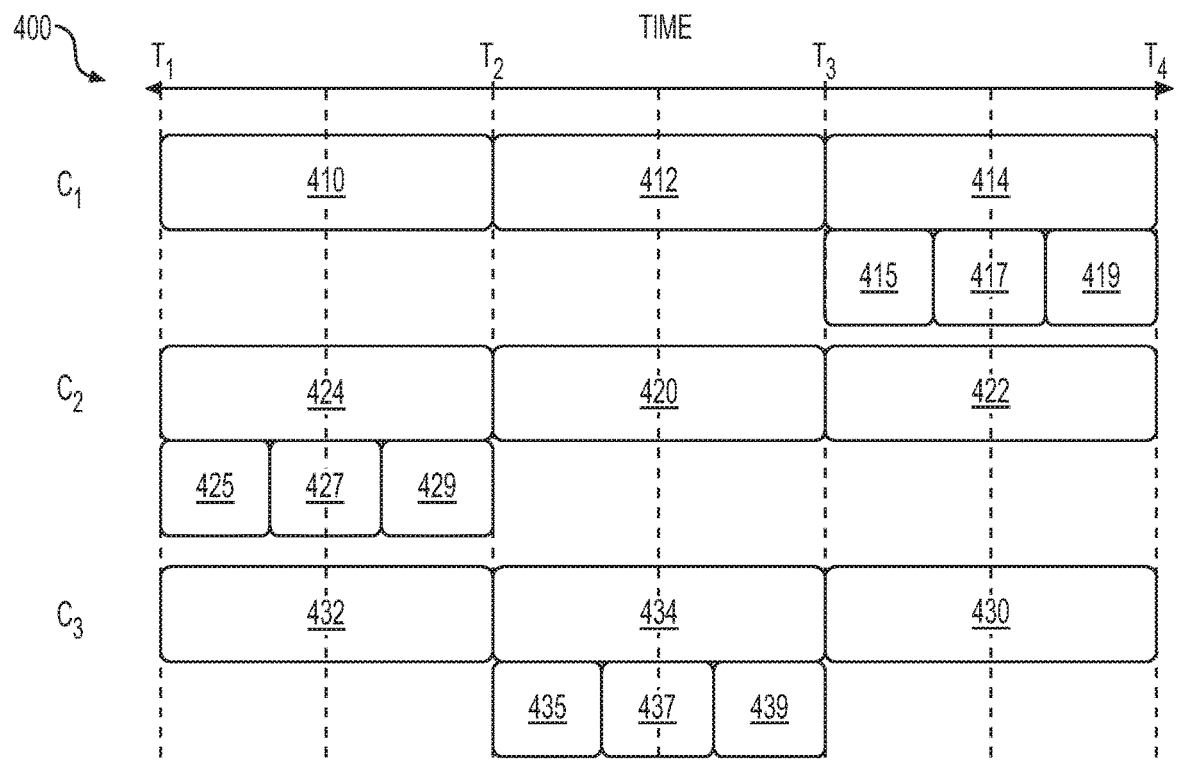
FIG. 3A is a graphical depiction of an exemplary method for preparing a target polypeptide according to some embodiments of the present disclosure.

FIG. 3A is a graphical depiction of a method according to some embodiments of the present disclosure. On the left axis of the graph, three separate rows are defined by the labels $C_1$, $C_2$, and $C_3$, representing a first column, a second column, and a third column of a HIC apparatus. The top axis represents time, extending indefinitely to the left and right. The continuous occupation of each column is exemplary of embodiments described herein; this arrangement reduces or eliminates idle time for columns (e.g., "dead time") as compared to conventional HIC methods. The segment of time shown in the entirety of FIG. 3A represents one exemplary cycle of a repeating pattern, which may repeat before and/or after the time segment shown in FIG. 3A. Four times are labeled as $T_1$, $T_2$, $T_3$, and $T_4$ and are examples of any line $T_0$ which may be drawn vertically through the graph. In some embodiments, the interval between $T_1$ and $T_2$ is substantially the same as the interval between $T_2$ and $T_3$, which in some embodiments, is substantially the same as the interval between $T_3$ and $T_4$. In some embodiments the interval between adjoining labeled times (e.g., between $T_1$ and $T_2$ or between $T_3$ and $T_4$) may be greater than or equal 30 seconds (s), less than or equal to 90 minutes (min), 30 s to 60 min, 30 s to 30 min, 30 s to 15 min, 30 s to 10 min, 30 s to 8 min, 30 s to 7 min, 30 s to 6 min, 30 s to 5 min, 30 s to 4 min, 30 s to 3 min, 1 min to 5 min, or 2 min to 5 min. The boxes 410, 412, 414, 415, 417, 419, 424, 420, 422, 424, 425, 427, 429, 430, 432, 434, 435, 437, and 439 represent an event occurring within each column, $C_1$, $C_2$, and $C_3$ in the time interval in which each box appears. For example, each box may represent the presence of a mixture, a mobile phase, or other resident liquid within the row of the column in which it appears.

Moving across FIG. 3A from left to right, progressing "forward" in time, from $T_1$ to $T_2$, a secondary load of the mixture may be in the first column $C_1$ (box 410). From $T_2$ to $T_3$, a primary load of the mixture may be in the first column $C_1$ (box 412), and from $T_3$ to $T_4$, one or more mobile phases may be in the first column $C_1$ (box 414). In some embodiments, a column may receive either a primary load of the mixture or a secondary load of the mixture. A "primary load" of the mixture refers to a load of the mixture passed to a column of the HIC apparatus without being first passed through another column of the HIC apparatus previously. A "secondary load" of the mixture refers to a load of the mixture passed via another column of the HIC apparatus prior to being introduced to a given column (e.g., an effluent from a primary load of the mixture is introduced to another column as a secondary load of the mixture). The passing of an effluent from one column to another with the effluent including the target peptide may allow for a column to be fully loaded without the concern of wasting overflow, and may increase the efficiency of the use of each column and may reduce the volume of hydrophobic interaction media consumed. By passing the overflow over hydrophobic interaction media which may have received or may receive a primary load of mixture including the target polypeptide, the volume of hydrophobic interaction media consumed relative to the amount of load mixture processed may be reduced.

In some embodiments, contacting one or more mobile phases to a column may include contacting a wash buffer to the column, contacting a stripping buffer to the column, and/or contacting an equilibration buffer to the column. In some embodiments, a wash buffer may comprise one or more salts such as, for example, sodium, potassium, magnesium, calcium, citrate, acetate, phosphate, sulfate, Tris, or other salt.

In some embodiments, a stripping buffer may comprise water, an alkaline solution, or a solution comprising alcohol. Deionized water, for example, may have less than 5 percent by volume (vol. %) dissolved ions, less than 1 vol. % dissolved ions, less than 0.1 vol. % dissolved ions, or even less than 0.01 vol. % dissolved ions. According to some embodiments, an alkaline solution may comprise one or more alkaline ionic compounds such as LiOH, NaOH, KOH, $Ca(OH)_2$, $NH_4OH$ or other alkaline compound. The concentration of alkaline compound in the stripping buffer may range, for example, from about 0.1 N to about 1.5 N, from about 0.1 N to about 1 N, from about 0.1 N to about 1.5 N, from about 0.5 N to about 1.5 N, from about 0.1 N to about 0.8 N, from about 0.1 N to about 0.6 N, from about 0.1 N to about 0.5 N, from about 0.1 N to about 0.4 N, or from about 0.1 N to about 0.3 N. For example, the concentration of alkaline compound in the stripping buffer may be about 0.1 N, about 0.2 N, about 0.3 N, about 0.4 N, about 0.5 N, about 0.6 N, about 0.7 N, about 0.8 N, about 0.9 N, about 1 N, about 1.1 N, about 1.2 N, about 1.3 N, about 1.4 N, or about 1.5 N. A stripping buffer comprising alcohol may include methanol, ethanol, propanol, benzyl alcohol, or other alcohol. The concentration of alcohol in the stripping buffer may range from about 0.1 vol. % to about 30 vol. %, such as from about 0.5 vol. % to about 30 vol. %, from about 0.5 vol. % to about 25 vol. %, from about 0.5 vol. % to about 25 vol. %, from about 0.5 vol. % to about 25 vol. %, from about 1 vol. % to abut 20 vol. %, from about 1 vol. % to about 15 vol. %, from about 1 vol. % to about 10 vol. %, from about 10 vol. % to about 50 vol. %, from about 10 vol. % to about 40 vol. %, from about 10 vol. % to about 30 vol. %, from about 10 vol. % to about 25 vol. %, from about 15 vol. % to about 25 vol. %, or from about 20 vol. % to about 25 vol. %, based on the total weight of the stripping buffer. For example, the concentration of alcohol in the stripping buffer may be about 0.1 vol. %, about 0.5 vol. %, about 1 vol. %, about 2 vol. %, about 3 vol. %, about 5 vol. %, about 10 vol. %, about 15 vol. %, about 20 vol. %, or about 25 vol. %.

In some embodiments, an equilibration buffer may be similar or identical in composition to the wash buffer. In other embodiments, the equilibration buffer may vary in composition compared to the wash buffer. In some embodiments, the equilibration buffer may comprise one or more salts such as, for example, sodium, potassium, magnesium, calcium, citrate, acetate, phosphate, sulfate, Tris, or other salt.

Referring to FIG. 3A, contacting one or more mobile phases in the first column 414 may be divided into separate phases including a wash buffer in the first column (box 415), a stripping buffer in the first column (box 417), and a equilibration buffer in the first column (box 419). In the next row (representing $C_2$), from $T_1$ to $T_2$, one or more mobile phases may be in the second column (box 424). This too may be divided into separate phases including a wash buffer in the second column (box 425), a stripping buffer in the second column (box 427), and an equilibration buffer in the second column (box 429). Moving to the right, from $T_2$ to $T_3$ a secondary load of a mixture may be in the second column (box 420), and from $T_3$ to $T_4$ a primary load of the mixture may be in the second column (box 422).

On the next row, from $T_1$ to $T_2$ a primary load of the mixture may be in the third column (box 432). Next, from $T_2$ to $T_3$, one or more mobile phases may be in the third column (box 434), and from $T_3$ to $T_4$ a secondary load of the mixture may be in the third column (box 430). The one or more mobile phases in the third column (box 434) may be divided into separate phases including a wash buffer in the third column (box 435), a stripping buffer in the third column (box 437), and an equilibration buffer in the third column (box 439).

At a given time $T_0$, a vertical line may be drawn through the graph such that each numbered box contacted by the vertical line from $T_0$ represents a solution in a column at that time. Thus, for example, at time $T_1$, the secondary load mixture is being introduced to the first column $C_1$ (box 410), one or more mobile phases are being passed to the second column $C_2$ (box 424), such as a wash buffer being passed to $C_2$ (box 425), and a primary load mixture is being passed to the third column $C_3$ (box 432). Although subdivisions of broader phases, such as, for example, subdivisions 425, 427, and 429 appear to occupy equal portions of the one or more mobile phases in the second column 424, in some embodiments, the subdivisions may occupy unequal portions of the broader phase. It should also be understood that the method depicted in FIG. 3A is but one exemplary progression according to embodiments of the present disclosure. Other orders, configurations, and steps are contemplated and considered within the scope of the present disclosure.

Figure 3B:
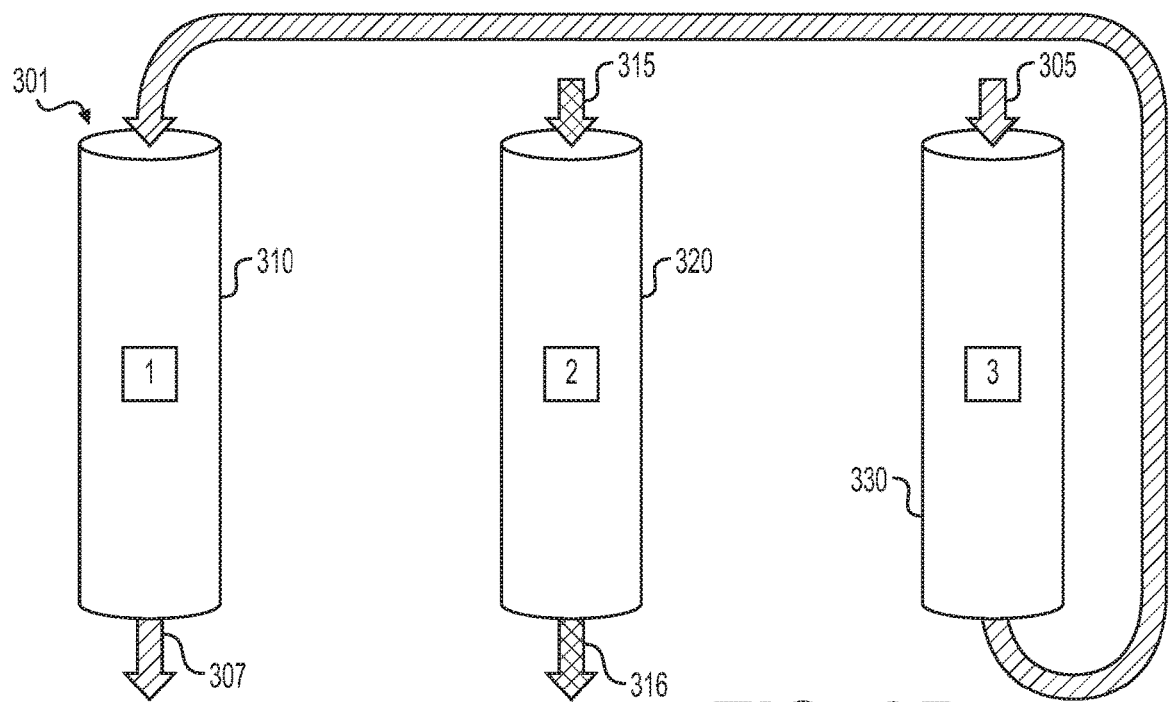
FIGS. 3B-3D are simplified illustrations depicting a method for preparing a target polypeptide, as shown in FIG. 3A.
Figure 3C:
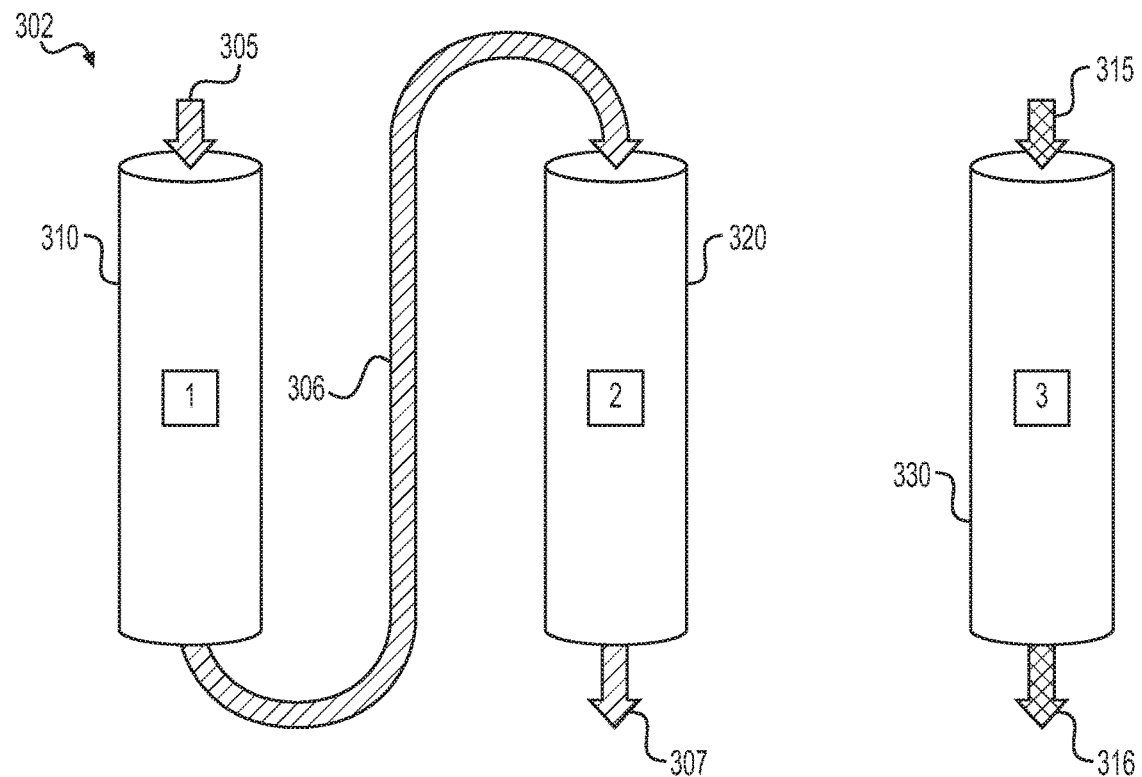
Figure 3D:
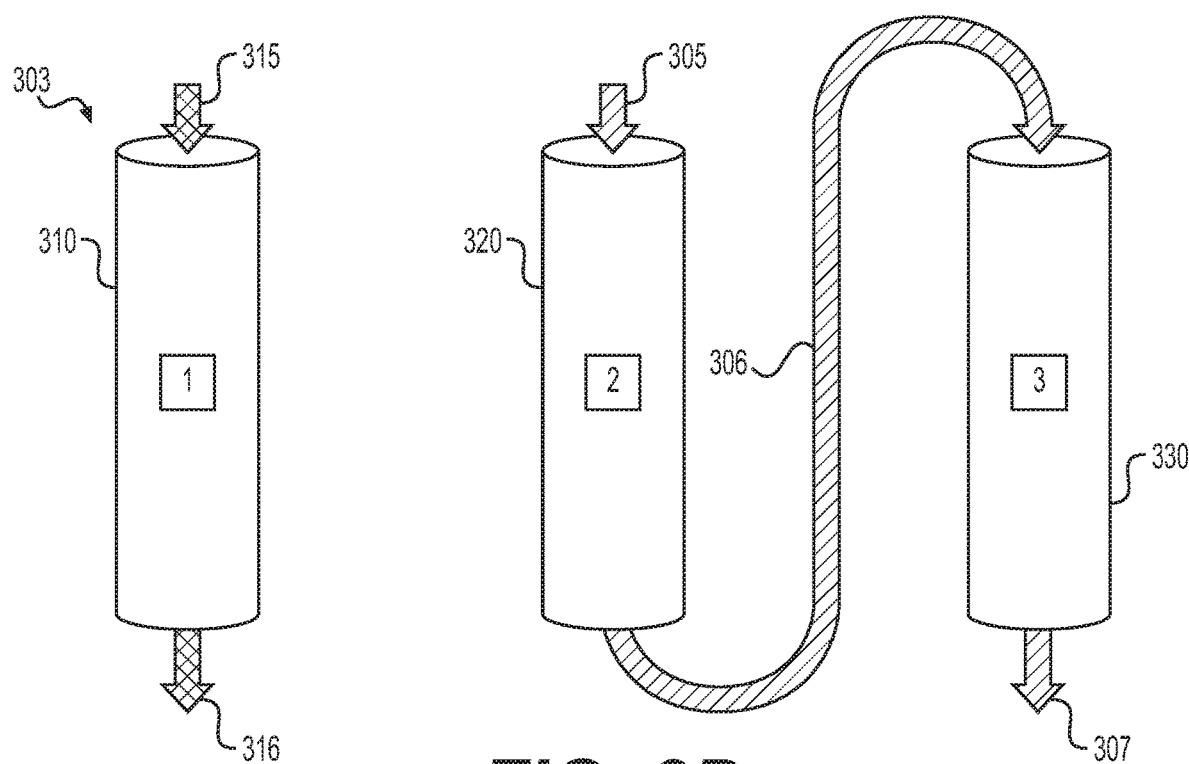

FIGS. 3B-3D illustrate an exemplary cycle for a method for preparing a target polypeptide from a mixture including the target polypeptide as previously described. FIG. 3B depicts a series of events that may occur during time interval $T_1$ to $T_2$, of FIG. 3A. Thus, FIG. 3B shows a HIC apparatus in a first stage 301 where a first zone 310 is receiving a secondary load of a mixture 306 including a target polypeptide and eluting an effluent of the secondary load 307 that may be collected or disposed. A second zone 320 is receiving one or more mobile phases 315 and eluting an effluent of the one or more mobile phases 316 that may be collected or disposed. A third zone 330 is receiving a primary load of a mixture 305 and passing a secondary load of a mixture 306 to another column.

FIG. 3C shows a HIC apparatus in a second stage 302 (over an interval $T_2$ to $T_3$, as shown in FIG. 3A) where a first zone 310 is receiving a primary load of a mixture 305 and passing a secondary load of a mixture 306 to another column. A second zone 320 is receiving a secondary load of a mixture 306 and eluting an effluent of the secondary load 307 that may be collected or disposed. A third zone 330 is receiving one or more mobile phases 315 and eluting an effluent of the one or more mobile phases 316 that may be collected or disposed.

FIG. 3D shows a HIC apparatus in a third stage 303 (over an interval $T_3$ to $T_4$, as shown in FIG. 3A) where a first zone 310 is receiving one or more mobile phases 315 and eluting an effluent of the one or more mobile phases 316 that may be collected or disposed. A second zone 320 is receiving a primary load of a mixture 305 and passing a second load of a mixture 306 to another column. A third zone 330 is receiving one or more mobile phases 315 and eluting an effluent of the one or more mobile phases 316 that may be collected or disposed.

Figure 4:
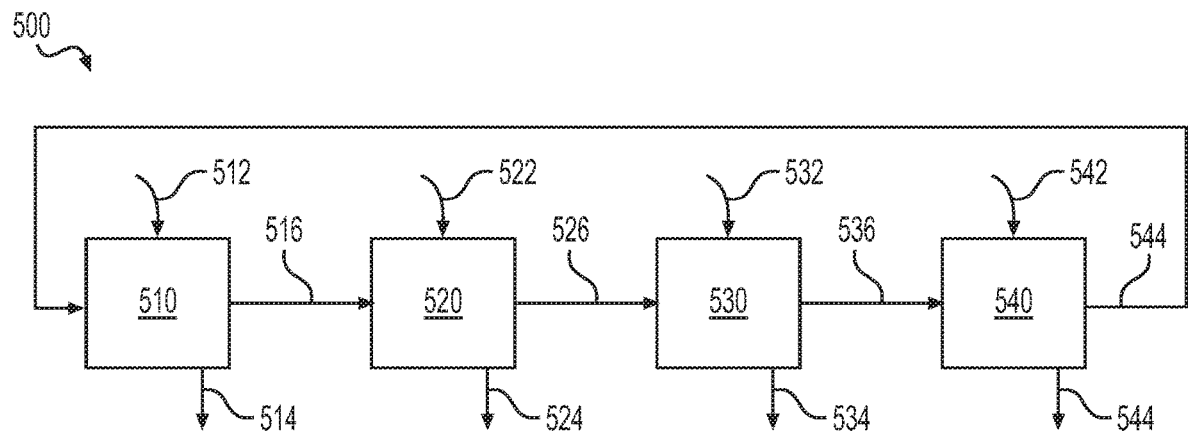
FIG. 4 is a schematic depiction of a chromatography apparatus, according to some embodiments of the present disclosure.

Another exemplary HIC apparatus 500 is schematically depicted in FIG. 4, according to some embodiments described herein. The HIC apparatus 500 may include a first zone 510, a second zone 520, a third zone 530, and a fourth zone 540. The first zone 510 may have a first inlet 512 configured such that a mixture including a target polypeptide, one or more mobile phases, or other liquids may be passed to the first zone 510. The first zone 510 may also have a first outlet 514 through which effluent (e.g., fluid which has passed through the first zone 510) may be passed from the HIC apparatus 500 to be collected or discarded. Effluent may also be passed from the first zone 510 to the second zone 520 via a first interconnect 516. The first zone 510 may also receive effluent from the fourth zone 540 via a fourth interconnect 546.

The second zone 520 may receive effluent from the first zone 510 via first interconnect 516. The second zone 520 may also have a second inlet 522 configured such that a mixture including a target polypeptide, one or more mobile phases, or other liquids may be passed to the second zone 520. The second zone 520 may also have a second outlet 524 through which effluent (e.g., fluid which has passed through the second zone 520) may be passed from the HIC apparatus 500 to be collected or discarded. Effluent may also be passed from the second zone 520 to the third zone 530 via a second interconnect 526.

The third zone 530 may receive effluent from the second zone 520 via second interconnect 526. The third zone 530 may have a third inlet 532 configured such that a mixture including a target polypeptide, one or more mobile phases, or other liquids may be passed to the third zone 530. The third zone 530 may also have an outlet 534 through which effluent (e.g., fluid which has passed through the third zone 530) may be passed from the HIC apparatus 500 to be collected or discarded. Effluent may also be passed from the third zone 530 to the fourth zone 520 via a third interconnect 536.

The fourth zone 540 may receive effluent from the third zone 530 via third interconnect 536. The fourth zone 540 may have a fourth inlet 542 configured such that a mixture including a target polypeptide, one or more mobile phases, or other liquids may be passed to the fourth zone 540. The fourth zone 540 may also have an outlet 544 through which effluent (e.g., fluid which has passed through the fourth zone 540) may be passed from the HIC apparatus 500 to be collected or discarded. Effluent may also be passed from the fourth zone 540 to the first zone 510 via a fourth interconnect 546.

Various components know to be used in chromatographic apparatuses (e.g., filters, sensors, gauges, thermometers) may be incorporated into a HIC apparatus 500, though not shown in the simplified schematic of FIG. 4. In some embodiments, one or more of a UV absorption, electrical conductivity, or pH or a resident solution may be measured at one or more points in the HIC apparatus 500. Suitable points for measuring UV absorption, electrical conductivity, or pH include at an inlet 512, 522, 532, 542 within a zone 510, 520, 530, 540 at an interconnect 516, 526, 536, 546 or at an outlet 514, 524, 534, 544. Inlets 512, 522, 532, 542 interconnects 516, 526, 536, 546 and outlets 514, 524, 534, 544 may be operable to move from an open configuration to a closed configuration: an open configuration allowing a fluid to pass through the inlet 512, 522, 532, 542, interconnect 516, 526, 536, 546, or outlet 514, 524, 534, 544 and a closed configuration not allowing a fluid to pass through the inlet 512, 522, 532, 542, interconnect 516, 526, 536, 546 or outlet 514, 524, 534, 544. A HIC apparatus 500 may include one or more pumps that provide pressure to transmit fluid between zones 510, 520, 530, 540, inlets 512, 522, 532, 542, interconnects 516, 526, 536, 546 and outlets 514, 524, 534, 544. In some embodiments, one or more interconnects 516, 526, 536, 546 may be moved to join different zones 510,

520, 530, 540. For example, during one or more chromatographic processes using HIC apparatus 500 it may be desirable to rearrange where interconnect 536 passes effluent from zone 530. In those situations, interconnect 536 may be reconfigured, without interrupting the chromatographic process, to pass effluent from zone 530 to zone 520. This is just one example, and in general, any interconnect 516, 526, 536, 546 may be reconfigured to connect different zones 510, 520, 530, 540 without interrupting an ongoing chromatographic process.

Figure 5A:
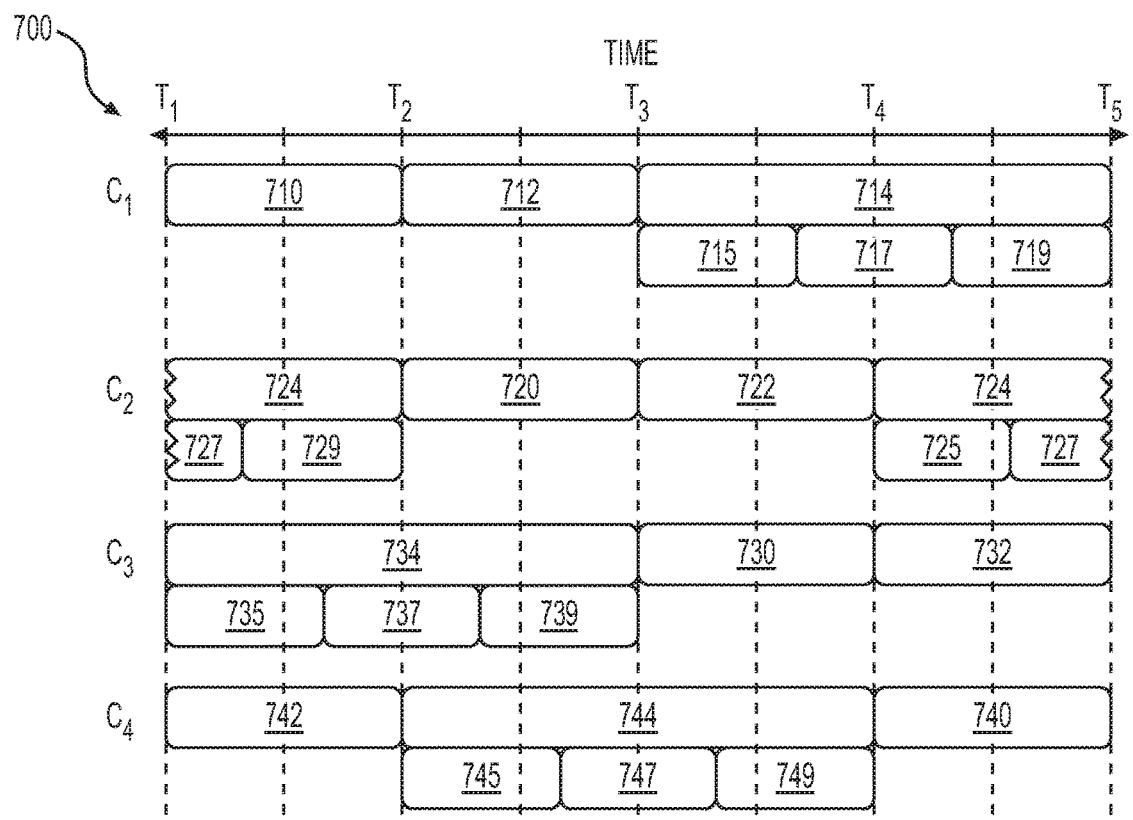
FIG. 5A is a graphical depiction of an exemplary method for preparing a target polypeptide according to some embodiments of the present disclosure.

FIG. 5A is a graphical depiction of one or more methods according to the present disclosure. On the left axis of the graph, four separate rows are defined by the labels $C_1$, $C_2$, $C_3$, and $C_4$ representing a first column, a second column, a third column, and a fourth column of a HIC apparatus. The top axis represents time, extending indefinitely to the left and right. The continuous occupation of each column is exemplary of embodiments described herein, this arrangement reduces or eliminates idle time for columns (e.g., "dead time") as compared to conventional HIC methods. The segment of time shown represents one cycle of a repeating pattern, understanding the pattern of numbered boxes, described below, may repeat on both sides of the segment shown in FIG. 5A. Five times are labeled as $T_1$, $T_2$, $T_3$, $T_4$, and $T_5$ and are examples of any line $T_0$ which may be drawn vertically through the graph. In some embodiments, the interval between $T_1$ and $T_2$ may be substantially the same as the interval between $T_2$ and $T_3$, which in some embodiments, may be substantially the same as the interval between $T_3$ and $T_4$, which in some embodiments may be substantially the same as the interval between $T_4$ and $T_5$. In some embodiments, intervals between each of these times may differ. In some embodiments the interval between adjoining labeled times (e.g., between $T_1$ and $T_2$ or between $T_4$ and $T_5$) may be greater than or equal 30 s, less than or equal to 90 min, 30 s to 60 min, 30 s to 30 min, 30 s to 15 min, 30 s to 10 min, 30 s to 8 min, 30 s to 7 min, 30 s to 6 min, 30 s to 5 min, 30 s to 4 min, 30 s to 3 min, 1 min to 5 min, or 2 min to 5 min. The boxes 710, 712, 714, 724, 720, 722, 734, 730, 732, 742, 744, and 740 represent a mixture, a buffer, or other resident liquid within each column, $C_1$, $C_2$, $C_3$, and $C_4$.

Moving across FIG. 5A from left to right, in the first row (representing the first column $C_1$), from $T_1$ to $T_2$, a secondary load of the mixture may be in the first column (box 710). From $T_2$ to $T_3$, a primary load of the mixture may be in the first column (box 712) and from $T_3$ to $T_5$ one or more mobile phases may be in in the first column (box 714).

Still referring to FIG. 5A, one or more mobile phases in the first column 714 may be divided into separate phases including a wash buffer in the first column (box 715), a stripping buffer in the first column (box 717), and a equilibration buffer in the first column (box 719). In the next row (representing the second column $C_2$), from $T_1$ to $T_2$, one or more mobile phases may be in the second column (box 724), continuing from $T_4$ to $T_5$ of the previous cycle. This too may be divided into separate phases including a wash buffer in the second column (box 725), a stripping buffer in the second column (box 727), and an equilibration buffer in the second column (box 729). Moving to the right, from $T_2$ to $T_3$ a secondary load of a mixture may be in the second column (box 720), and from $T_3$ to $T_4$ a primary load of the mixture may be in the second column (box 722).

On the next row (representing column $C_3$), from $T_1$ to $T_3$ one or more mobile phases may be in the third column (box 734). The one or more mobile phases in the third column 734 may be divided into separate phases including a wash buffer in the third column (box 735), a stripping buffer in the third column (box 737), and an equilibration buffer in the third column (box 739). Next, from $T_3$ to $T_4$, a secondary load may be in the third column (box 730), and from $T_4$ to $T_5$ a primary load of the mixture may be in the third column (box 732).

On the next row (representing column $C_4$), from $T_1$ to $T_2$ a primary load of the mixture may be in the fourth column (box 742). Next, from $T_2$ to $T_4$, one or more mobile phases may be in the fourth column (box 744), and from $T_4$ to $T_5$ a secondary load of the mixture may be in the third column (box 740). The one or more mobile phases in the fourth column 744 may be divided into separate phases including a wash buffer in the third column (box 745), a stripping buffer in the third column (box 747), and an equilibration buffer in the third column (box 749).

At a given time $T_0$, a vertical line may be drawn through the graph such that each numbered box contacted by the vertical line from $T_0$ represents a solution in a column at that time. So, for example, at time $T_1$, the secondary load mixture is being introduced to the first column 710, one or more mobile phases are in the second column 724, such as a stripping buffer 727, and a primary load mixture is being passed to the third column 732. It should be noted that although subdivisions of broader phases, such as, for example, subdivisions 725, 727, and 729 appear to occupy equal portions of the one or more mobile phases in the second column 724, in some embodiments, the subdivisions may occupy unequal portions of the broader phase. It should also be understood that the method depicted in FIG. 5A is but one example of the embodiment methods. Other orders, configurations, and steps are contemplated and considered within the scope of the present disclosure.

Figure 5B:
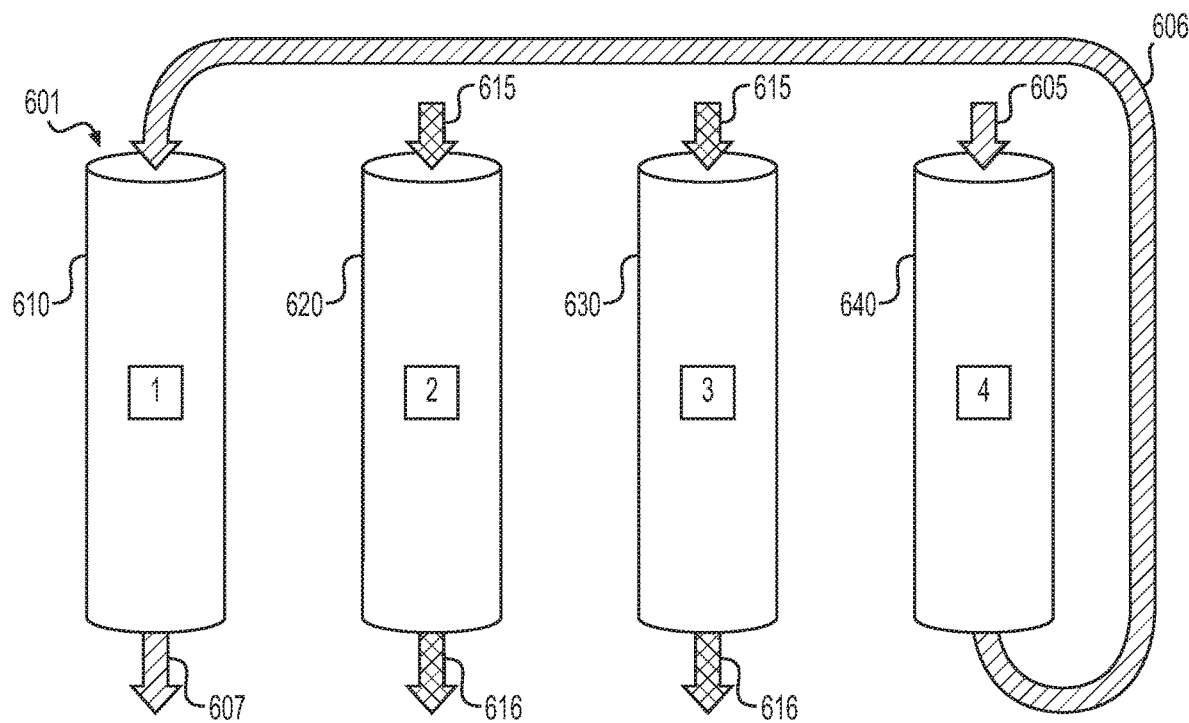
FIGS. 5B-5E are simplified illustrations depicting a method for preparing a target polypeptide, as shown in FIG. 5A.

FIGS. 5B-5E illustrate an exemplary cycle for a method for preparing a target polypeptide from a mixture including the target polypeptide as previously described. FIG. 5B depicts a series of events that occur in an interval $T_1$ to $T_2$ of FIG. 5A. FIG. 5B shows a HIC apparatus in a first stage 601 where a first zone 610 is receiving a secondary load of a mixture 606 including a target polypeptide and eluting an effluent of the secondary load 607 that may be collected or disposed. A second zone 620 is receiving one or more mobile phases 615 and eluting an effluent of the one or more mobile phases 616 that may be collected or disposed. A third zone 630 is receiving one or more mobile phases 615 and eluting an effluent of the one or more mobile phases 616 that may be collected or disposed. A fourth zone 640 is receiving a primary load of a mixture 605 and passing a secondary load of a mixture 606 to another column.

Figure 5C:
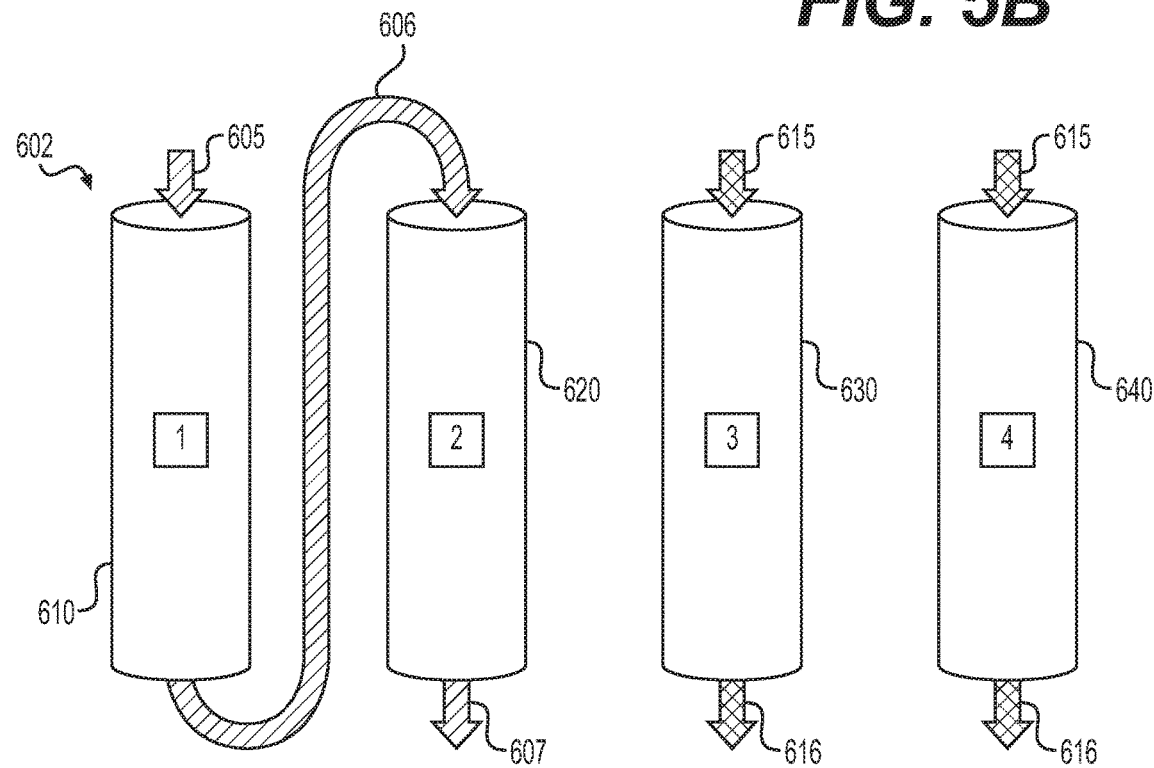

FIG. 5C shows a HIC apparatus in a second stage 602 (over an interval $T_2$ to $T_3$, as shown in FIG. 5A) where a first zone 610 is receiving a primary load of a mixture 605 and passing a secondary load of a mixture 606 to another column including a target polypeptide. that may be collected or disposed. A second zone 620 is receiving a secondary load of a mixture 606 including a target polypeptide and eluting an effluent of the secondary load 607 that may be collected or disposed. A third zone 630 is receiving one or more mobile phases 615 and eluting an effluent of the one or more mobile phases 616 that may be collected or disposed. A fourth zone 640 is receiving one or more mobile phases 615 and eluting an effluent of the one or more mobile phases 616 that may be collected or disposed.

Figure 5D:
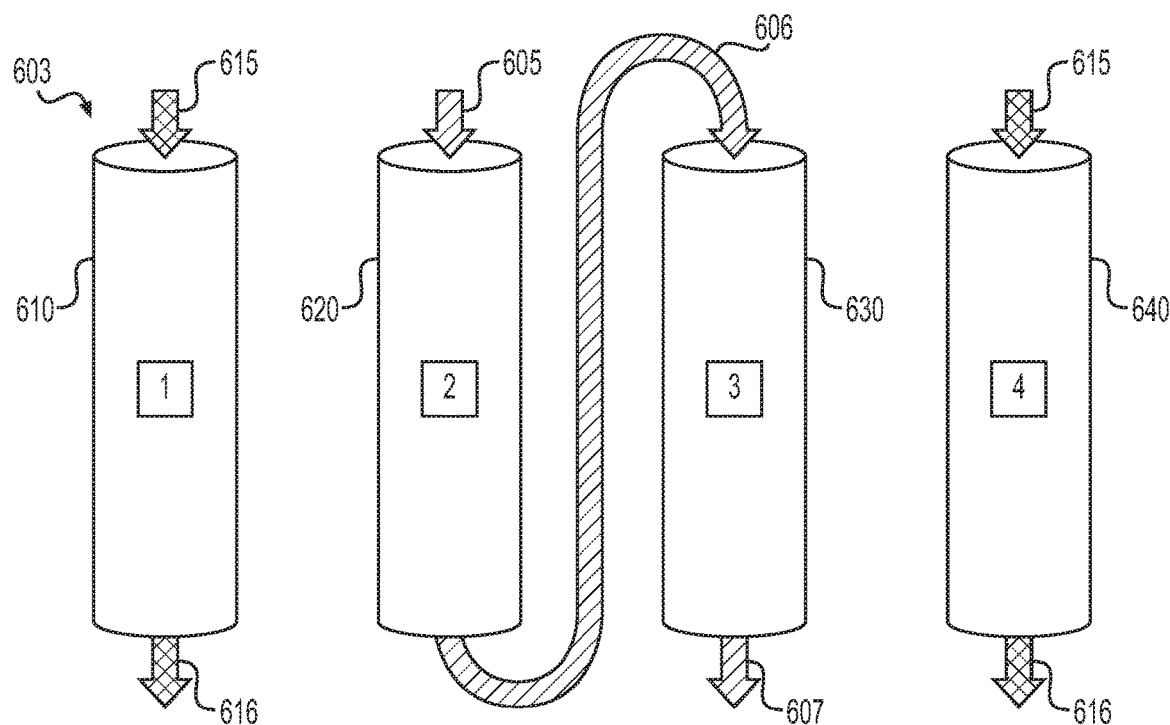

FIG. 5D shows a HIC apparatus in a third stage 603 (over an interval $T_2$ to $T_3$, as shown in FIG. 5A) where a first zone 610 is receiving one or more mobile phases 615 and eluting an effluent of the one or more mobile phases 616 that may be collected or disposed. A second zone 620 is receiving a primary load of a mixture 605 and passing a secondary load of a mixture 606 to another column including a target polypeptide. that may be collected or disposed. A third zone 630 is receiving a secondary load of a mixture 606 including a target polypeptide and eluting an effluent of the secondary load 607 that may be collected or disposed. A fourth zone 640 is receiving one or more mobile phases 615 and eluting an effluent of the one or more mobile phases 616 that may be collected or disposed.

Figure 5E:
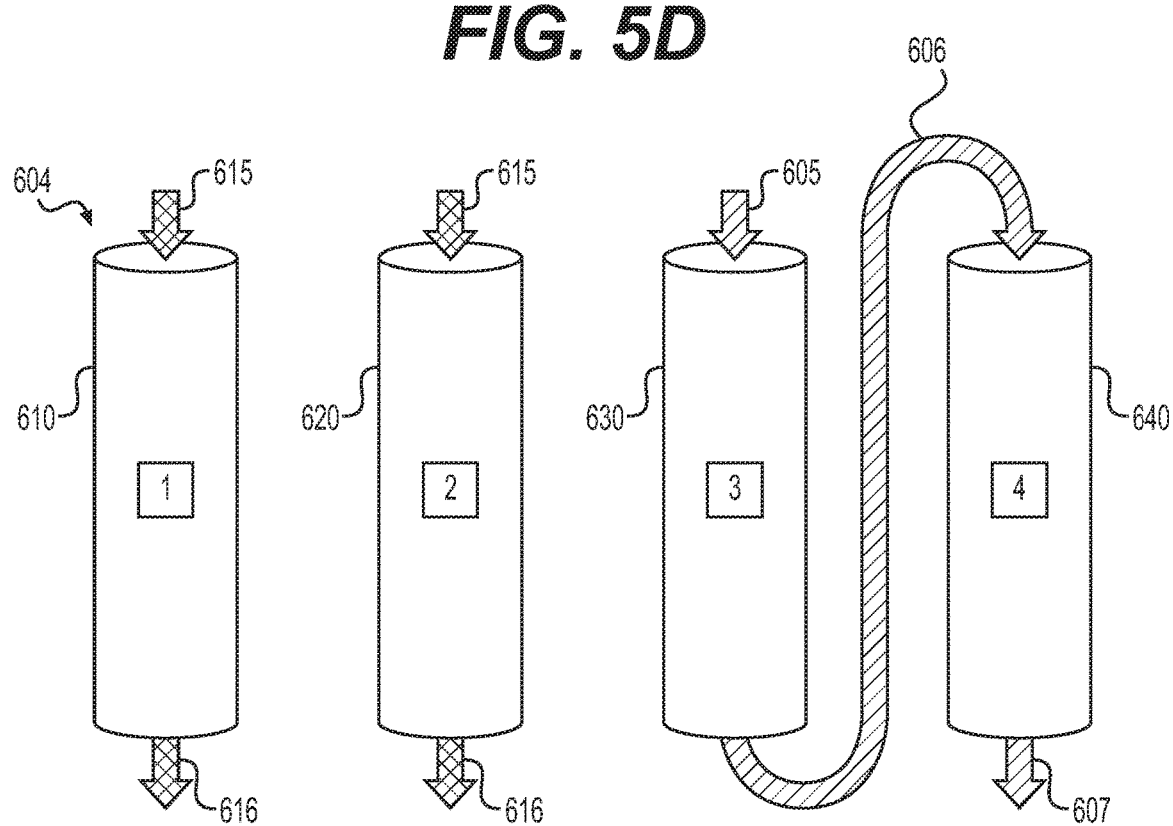

FIG. 5E shows a HIC apparatus in a fourth stage 604 (over an interval $T_2$ to $T_3$, as shown in FIG. 5A) where a first zone 610 is receiving one or more mobile phases 615 and eluting an effluent of the one or more mobile phases 616 that may be collected or disposed. A second zone 620 is receiving one or more mobile phases 615 and eluting an effluent of the one or more mobile phases 616 that may be collected or disposed. A third zone 630 is receiving a primary load of a mixture 605 and passing a secondary load of a mixture 606 to another column including a target polypeptide. that may be collected or disposed. A fourth zone 640 is receiving a secondary load of a mixture 606 including a target polypeptide and eluting an effluent of the secondary load 607 that may be collected or disposed.

Figure 6:
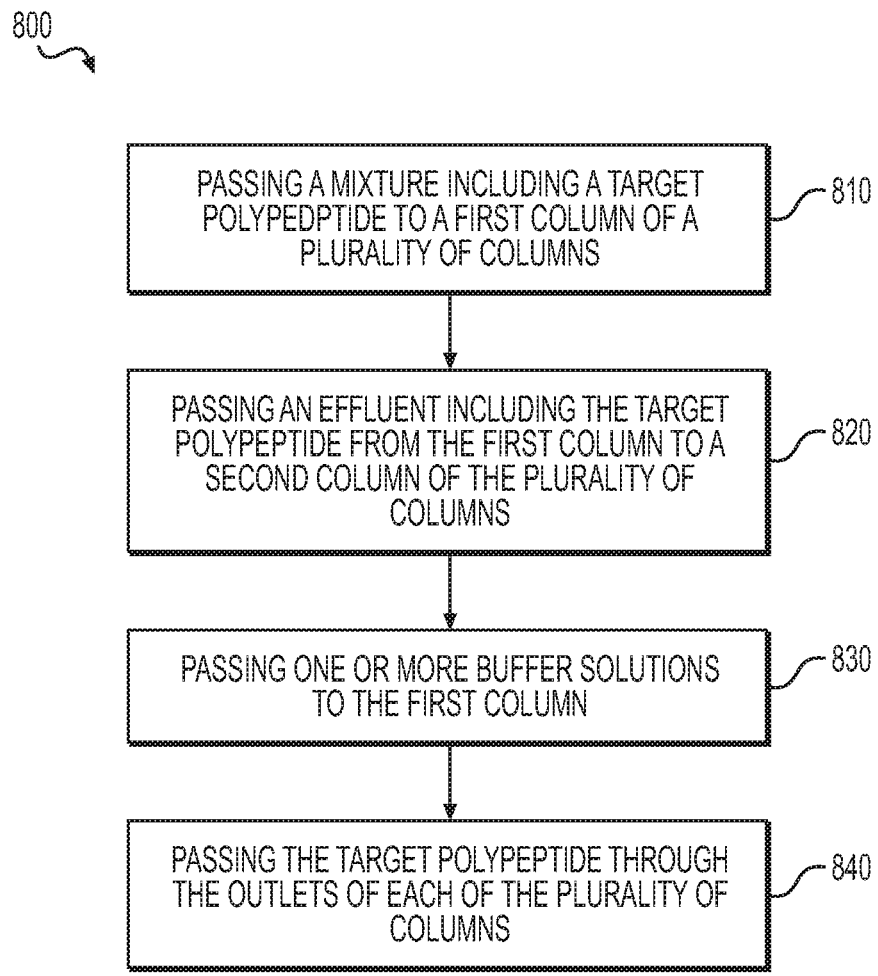
FIG. 6 is a flowchart of a method for preparing a target polypeptide according to some embodiments of the present disclosure.

FIG. 6 depicts a flow chart of an exemplary method 800 of preparing a target polypeptide from a mixture including a target polypeptide. The method may include passing a mixture including a target polypeptide to a first column of a plurality of columns (e.g., box 410 of FIG. 3A) (step 810). The method may further include passing an effluent including the target polypeptide from the first column to a second column of the plurality of columns (e.g., a second load of a mixture 306, as shown in FIG. 3B) (step 820). The method may further comprise passing one or more mobile phases to the first column (e.g., box 414) (step 830). In some embodiments, the method may further include passing the target polypeptide through the outlets of each of the plurality of columns (e.g., effluent of the one or more mobile phases 316, as shown in FIGS. 3B-3D) (step 840). While comparison is being made to FIGS. 3A-3D, it will be apparent to one of ordinary skill in the art that comparisons may also be made to FIGS. 5A-5E.

In embodiments of the present disclosure, a mixture containing a target polypeptide may also comprise one or more HCPs. After a target polypeptide is prepared from the mixture using one or more embodiment methods, several effluent samples may be obtained. The samples may be collected from effluent of one or more loads of the mixture and/or the effluent of one or more mobile phases. For example, the samples may be collected from effluent of a primary load of the mixture or a secondary load of the mixture (or any other load of the mixture). In some embodiments, samples may be only collected from the effluent of one or more wash buffers. In other embodiments, samples may be collected from the effluent of other mobile phases and/or the primary or secondary load of the mixture. The aggregate collection of all samples collected that contain the target polypeptide is referred to as the pool.

In some embodiments, one or more measurements may be taken to ascertain an efficiency of the employed method of preparing a target polypeptide. As used in this disclosure, efficiency refers to a combination of three different factors: high molecular weight molecule clearance factor (HMW CF), yield, and productivity. In some embodiments, a more efficient method has a higher HMW CF, a higher yield, and a higher productivity than the less efficient method. In other embodiments, a more efficient method has a higher productivity than the less efficient method, while maintaining a HMW CF greater than or equal to 1.3 and maintaining a yield greater than or equal to 80%. In further embodiments, a more efficient method has a higher productivity than the less efficient method, while maintaining a HMW CF greater than or equal to 1.5 and maintaining a yield greater than or equal to 90%.

High molecular weight molecule clearance factor (HMW CF) is an approximation of the relative protein content in a collected pool as compared to the loaded mixture. In some embodiments, analytical size exclusion chromatography may be performed to determine the percentage of a sample attributable to high molecular weight molecules (e.g., proteins) (HMW %). In other embodiments, a centrifuge technique may be used—as a sample is centrifuged it separates into strata based on the mass of the constituent components of the sample, the heaviest stratum, the infranatant, generally contains the heaviest molecules including proteins. The HMW % may be calculated by massing the infranatant of a centrifuged sample and dividing by the total mass of the sample. Using either method, the HMW CF may be calculated according to Equation 1, as shown below.

$$HMW\ CF = \frac{HMW\%_{load}}{HMW\%_{pool}} \qquad \text{Eq. (1)}$$

As shown in Eq. (1), a HMW CF may be calculated by dividing the HMW % of the loaded mixture by the HMW % of the pool. In some embodiments, a method of preparing a target polypeptide from a mixture has a HMW CF greater than or equal to 1.3. In other embodiments, a method of preparing a target polypeptide from a mixture has a HMW CF greater than or equal to 1.4, greater than or equal to 1.5, greater than or equal to 1.6, greater than or equal to 1.8, or greater than or equal to 2.0.

Yield is a measurement of the amount of target polypeptide collected in the pool compared to how much target polypeptide was in loading mixture. The amount of a target polypeptide in a sample may be quantified by UV absorption, electrical conductivity, or enzymatic immunoassay (e.g., ELISA). Yield may be calculated according to Equation 2, as shown below.

$$\text{Yield (\%)} = \left(\frac{Mass_{pool}}{Mass_{load}}\right) \times 100 = \left(\frac{(Conc_{pool})(Vol_{pool})}{(Conc_{load})(Vol_{load})}\right) \times 100 \qquad \text{Eq. (2)}$$

As shown in Eq. 2, yield may be calculated by dividing the mass of target polypeptide loaded into the HIC apparatus by the mass of target polypeptide collected in the pool. As the mass of target polypeptide in a sample cannot be directly measured, a concentration (calculated by UV absorption, electrical conductivity, or enzymatic immunoassay) may be multiplied by a volume to determine a mass. In some embodiments, a method of preparing a target polypeptide from a mixture has a yield greater than or equal to 55%. In other embodiments, a method of preparing a target polypeptide from a mixture has a yield greater than or equal to 60%, greater than or equal to 65%, greater than or equal to 70%, greater than or equal to 75%, greater than or equal to 80%, great than or equal to 85%, greater than or equal to 90%, or greater than or equal to 95%.

Productivity is a quantification of the time and cost need to prepare an amount of target polypeptide. Productivity may be calculated according to Equation 3, as shown below.

$$\text{Productivity} = \frac{Mass_{pool}}{Vol_{medium} \times (CycleTime \times No. \text{ of cycles})} \quad \text{Eq. (3)}$$

As shown in Eq. 3, productivity may be calculated by dividing the mass of target polypeptide collected in the pool by the product of the volume of hydrophobic interaction medium used and the time elapsed to prepare the mass of polypeptide collected in the pool (e.g., cycle time). In some embodiments, a method of preparing a target polypeptide from a mixture has a productivity of greater than or equal to about 35 g/L·hr. In other embodiments, a method of preparing a target polypeptide from a mixture has a productivity of greater than or equal to about 40 g/L·hr, greater than or equal to about 50 g/L·hr, greater than or equal to about 75 g/L·hr, greater than or equal to about 100 g/L·hr, greater than or equal to about 125 g/L·hr, greater than or equal to about 150 g/L·hr, greater than or equal to about 175 g/L·hr, greater than or equal to about 200 g/L·hr, or greater than or equal to about 220 g/L·hr.

EXAMPLES

The following examples are intended to illustrate the present disclosure without being limiting in nature. It is understood that the present disclosure encompasses additional aspects and embodiments consistent with the foregoing description and following examples.

In some of the following examples, reference is made to "continuous chromatography" or "continuous HIC." These terms refer to protocols and/or apparatuses including two or more chromatography columns (e.g., HIC columns), each of which may be in a different portion of a repeating chromatography cycle passing through all of the columns. Embodiments of the present disclosure (e.g., depicted in FIGS. 2-5E) are examples of continuous chromatography and/or continuous HIC. Continuous chromatography (e.g., continuous HIC) protocols may be characterized by an aim to lower or eliminate column idle time (also referred to as "dead time") as compared to conventional batch chromatography.

In the following examples, target polypeptides were prepared from a mixture including the target polypeptide and HCP, using several different methods according to embodiments of the present disclosure. Several target polypeptide pools were also prepared using a conventional batch processing method as comparative examples.

Example 1

In a first example, a target antibody was prepared. 300 mL of a 12.2 g/L mixture including a target antibody was loaded into a three-column HIC apparatus at a loading flow rate of 1.67 mL/min, where each column had a 2.5 cm bed height, a 1.6 cm inner diameter, and a column volume of 5 mL. The loading buffer/mixture included a 30 millimolar (mM) solution of sodium citrate and was adjusted to a pH of 6.0 with a 2M acetic acid solution. The loading buffer/mixture was loaded into a first and second column of the three columns. The second column was loaded via the first column (i.e., an outlet from the first column allowed loading buffer to pass into the second column). After the mixture was loaded into the first and second columns of the HIC apparatus, the mixture was loaded into the second and a third of the three columns, with the third column being loaded via the second column (i.e., an outlet from the second column allowed loading buffer to pass into the third column).

While the loading buffer/mixture was loading into the second and third columns, a series of mobile phases was passed to the first column of the HIC apparatus to separate the target antibody from other components of the mixture in the first column and collect the target antibody, followed by a series of stripping buffers passed to the first column to regenerate the column. Loading of the second and third columns occurred simultaneously with washing and stripping of the first column. After this step, the loading buffer/mixture was loaded into the third and first columns, with the first column being loaded via the third column (i.e., an outlet from the third column allowed loading buffer to pass into the first column), during which buffers were passed to the second column to separate and collect the target antibody from the mixture loaded in the second column, after which the series of stripping buffers were passed to the second column to regenerate the second column. Loading of the third and first columns occurred simultaneously with washing and stripping of the second column. Finally, the loading buffer/mixture was loaded into the first and second columns again, with the second column being loaded via the first column as previously described, during which buffers were passed to the third column to separate and collect the target antibody from the mixture loaded in the third column, after which the series of stripping buffers were passed to the third column to regenerate the third column. Loading of the first and second columns occurred simultaneously with washing and stripping of the third column. This process was repeated cyclically twice.

The series of mobile phases included a wash buffer, a series of stripping buffers, and an equilibration buffer. The wash buffer included 40 mM Tris and 30 mM sodium citrate and was adjusted to a pH of 6.0. For washing each column, four column volumes of wash buffer were added to the column.

After the wash buffer was applied and the effluent including the target antibody was collected from a column as part of the pool, a series of stripping buffers was passed to the column as part of the column regeneration process. The first stripping buffer included deionized water, two columns volumes of this buffer were added to each column. As used herein, a column volume refers to the volume of liquid the given column can retain. The next stripping buffer include 1 N NaOH, two column volumes of this buffer were added to each column after the first stripping buffer. The next stripping buffer comprised deionized water, two column volumes of this buffer were added to each column after the previous alkaline stripping buffer. The next stripping buffer included 20 vol. % ethanol and two column volumes of this buffer were added to each column after the previous deionized water stripping buffer. A final stripping buffer, including deionized water, was added to the column (in an amount equal to two column volumes). After the stripping buffers were applied, four column volumes of an equilibration buffer were added to the column. The equilibration buffer included 40 mM Tris and 30 mM sodium citrate and was adjusted to a pH of 6.0.

After the pool was collected from the method run in Example 1, the HMW CF, yield, and productivity of the method were measured and calculated as previously described herein. The results are summarized below in Table 1.

Example 2

In a second example, a target antibody was prepared. 729 mL of a 12.4 g/L mixture including a target polypeptide was loaded into a three column HIC apparatus at a loading flow rate of 1.67 mL/min, where each column had a 2.5 cm bed height, a 1.6 cm inner diameter, and a column volume of 5 mL. The loading buffer/mixture included a 30 millimolar (mM) solution of sodium citrate and was adjusted to a pH of 6.0 with a 2M acetic acid solution. The loading buffer/mixture was loaded into a first and second column of the three columns. The second column was loaded via the first column (i.e., an outlet from the first column allowed loading buffer to pass into the second column). After the mixture was loaded into the first and second columns of the HIC apparatus, the mixture was loaded into the second and a third of the three columns, with the third column being loaded via the second column (i.e., an outlet from the second column allowed loading buffer to pass into the third column).

While the loading buffer/mixture was loading into the second and third columns, a series of mobile phases was passed to the first column of the HIC apparatus to separate the target antibody from other components of the mixture in the first column and collect the target antibody, followed by a series of stripping buffers passed to the first column to regenerate the column. Loading of the second and third columns occurred simultaneously with washing and stripping of the first column. After this step, the loading buffer/mixture was loaded into the third and first columns, with the first column being loaded via the third column (i.e., an outlet from the third column allowed loading buffer to pass into the first column), during which buffers were passed to the second column to separate and collect the target antibody from the mixture loaded in the second column, after which the series of stripping buffers were passed to the second column to regenerate the second column. Loading of the third and first columns occurred simultaneously with washing and stripping of the second column. Finally, the loading buffer/mixture was loaded into the first and second columns again, with the second column being loaded via the first column as previously described, during which buffers were passed to the third column to separate and collect the target antibody from the mixture loaded in the third column, after which the series of stripping buffers were passed to the third column to regenerate the third column. Loading of the first and second columns occurred simultaneously with washing and stripping of the third column. This process was repeated cyclically four times.

The series of mobile phases included a wash buffer, a series of stripping buffers, and an equilibration buffer. The wash buffer included 40 mM Tris and 30 mM sodium citrate and was adjusted to a pH of 6.0. For washing each column, four column volumes of wash buffer were added to the column.

After the wash buffer was applied and the effluent including the target antibody was collected from a column as part of the pool, a series of stripping buffers was passed to the column as part of the column regeneration process. The first stripping buffer included deionized water, two columns volumes of this buffer were added to each column. As used herein, a column volume refers to the volume of liquid the given column can retain. The next stripping buffer include 1 N NaOH, two column volumes of this buffer were added to each column after the first stripping buffer. The next stripping buffer comprised deionized water, two column volumes of this buffer were added to each column after the previous alkaline stripping buffer. The next stripping buffer included 20 vol. % ethanol and two column volumes of this buffer were added to each column after the previous deionized water stripping buffer. A final stripping buffer, including deionized water, was added to the column (in an amount equal to two column volumes). After the stripping buffers were applied, four column volumes of an equilibration buffer were added to the column. The equilibration buffer included 40 mM Tris and 30 mM sodium citrate and was adjusted to a pH of 6.0.

After the pool was collected from the method run in Example 2, the HMW CF, yield, and productivity were measured and calculated as previously described herein. The results are summarized below in Table 1.

Example 3

In a third example, a target polypeptide was prepared. 726 mL of a 12.4 g/L mixture including a target polypeptide was loaded into a three column HIC apparatus at a loading flow rate of 6.70 mL/min, where each column had a 2.5 cm bed height, a 1.6 cm inner diameter, and a column volume of 5 mL. The loading buffer/mixture included a 30 millimolar (mM) solution of sodium citrate and was adjusted to a pH of 6.0 with a 2M acetic acid solution. The loading buffer/mixture was loaded into a first and second column of the three columns. The second column was loaded via the first column (i.e., an outlet from the first column allowed loading buffer to pass into the second column). After the mixture was loaded into the first and second columns of the HIC apparatus, the mixture was loaded into the second and a third of the three columns, with the third column being loaded via the second column (i.e., an outlet from the second column allowed loading buffer to pass into the third column).

While the loading buffer/mixture was loading into the second and third columns, a series of mobile phases was passed to the first column of the HIC apparatus to separate the target antibody from other components of the mixture in the first column and collect the target antibody, followed by a series of stripping buffers passed to the first column to regenerate the column. Loading of the second and third columns occurred simultaneously with washing and stripping of the first column. After this step, the loading buffer/mixture was loaded into the third and first columns, with the first column being loaded via the third column (i.e., an outlet from the third column allowed loading buffer to pass into the first column), during which buffers were passed to the second column to separate and collect the target antibody from the mixture loaded in the second column, after which the series of stripping buffers were passed to the second column to regenerate the second column. Loading of the third and first columns occurred simultaneously with washing and stripping of the second column. Finally, the loading buffer/mixture was loaded into the first and second columns again, with the second column being loaded via the first column as previously described, during which buffers were passed to the third column to separate and collect the target antibody from the mixture loaded in the third column, after which the series of stripping buffers were passed to the third column to regenerate the third column. Loading of the first and second columns occurred simultaneously with washing and stripping of the third column. This process was repeated cyclically four times.

The series of mobile phases included a wash buffer, a series of stripping buffers, and an equilibration buffer. The wash buffer included 40 mM Tris and 30 mM sodium citrate and was adjusted to a pH of 6.0. For washing each column, four column volumes of wash buffer were added to the column.

After the wash buffer was applied and the effluent including the target antibody was collected from a column as part of the pool, a series of stripping buffers was passed to the column as part of the column regeneration process. The first stripping buffer included deionized water, two columns volumes of this buffer were added to each column. As used herein, a column volume refers to the volume of liquid the given column can retain. The next stripping buffer include 1 N NaOH, two column volumes of this buffer were added to each column after the first stripping buffer. The next stripping buffer comprised deionized water, two column volumes of this buffer were added to each column after the previous alkaline stripping buffer. The next stripping buffer included 20 vol. % ethanol and two column volumes of this buffer were added to each column after the previous deionized water stripping buffer. A final stripping buffer, including deionized water, was added to the column (in an amount equal to two column volumes). After the stripping buffers were applied, four column volumes of an equilibration buffer were added to the column. The equilibration buffer included 40 mM Tris and 30 mM sodium citrate and was adjusted to a pH of 6.0.

After the pool was collected from the method run in Example 3, the HMW CF, yield, and productivity were measured and calculated as previously described herein. The results are summarized below in Table 1.

Comparative Example A

A target polypeptide was prepared from a mixture using a conventional batch process as described herein, as a comparison to the methods of Examples 1-3. The loading additives, wash buffer, stripping buffers, and equilibration buffers were identical to those used in the Example methods, but a conventional batch methodology was employed. 590 g of a 13.1 g/L load mixture was added to a chromatographic column. After the mixture passed through the column, 4 column volumes of wash buffer were added to the column and the effluent was collected. After a pool was collected from the comparative example method, the HMW CF, yield, and productivity were characterized. The results are summarized in Table 1.

TABLE 1

| Value | Example 1 | Example 2 | Example 3 | Comparative Example A |
|---|---|---|---|---|
| Volume of Hydrophobic Interaction Media used | 15 mL | 15 mL | 15 mL | 6.53 L |
| Loading rate | 1.67 mL/min | 1.67 mL/min | 6.70 mL/min | 1.05 L/min |
| Cycle Time | 3.01 hr | 2.44 hr | 0.61 hr | 2.26 hr |
| Load Concentration | 12.2 g/L | 12.4 g/L | 12.4 g/L | 13.1 g/L |
| Load Volume | 300 mL | 726 mL | 726 mL | 45.0 L |
| Load Mass | 3.66 g | 9.00 g | 9.00 g | 590 g |
| Load HMW % | 2.05% | 2.01% | 2.29% | 1.71% |
| Pool HMW % | 1.10% | 1.10% | 1.46% | 0.68% |
| Pool Concentration | 8.07 g/L | 9.06 g/L | 9.69 g/L | 9.75 g/L |
| Pool Volume | 359 mL | 687 mL | 844 mL | 58.5 L |
| Pool Mass | 2.90 g | 6.22 g | 8.18 g | 570.4 g |
| HMW CF | 1.9 | 1.8 | 1.6 | 2.5 |
| Yield | 79.2% | 68.7% | 90.9% | 96.7% |
| Productivity | 32.1 g/L · hr | 42.5 g/L · hr | 223.5 g/L · hr | 38.7 g/L · hr |

As can be seen from the data in table 1, Examples 2 and 3 have a higher productivity than the comparative example batch method. Additionally, Example 3 was able to achieve a higher productivity than the other examples while still maintaining a HMW CF greater than or equal to 1.5 and maintaining a yield greater than or equal to 90%.

Example 4

A target antibody was prepared using HIC with three different loading velocities to compare impurity break-throughs at the varying velocities. A column was prepared as described in Table 2:

TABLE 2

| | |
|---|---|
| Load Material | 30 mM Citrate; pH 6.0 +/− 0.1 |
| Column Bed Height | 20 cm |
| Column Inner Diameter | 1 cm |
| Column Packed Volume | 15.7 mL |
| Loading Concentration | 400 g/L total; after 100 g/L, fractionated every 25 g/L |
| Cleaning | Reverse osmosis deionized water; 1N NaOH; Reverse osmosis deionized water; 20% EtOH |

The loading velocities, in the order run, were 300 cm/h (3.93 mL/min, or a 4.0 min residence time in the column), 200 cm/hr (2.62 mL/min, or 6.0 min residence time in the column), and 400 cm/hr (5.24 mL/min, or 3.0 min residence time in the column). All runs were performed in the same column. An overnight soak was performed before the 400 cm/hr run in 0.5 N NaOH.

Figure 7A:
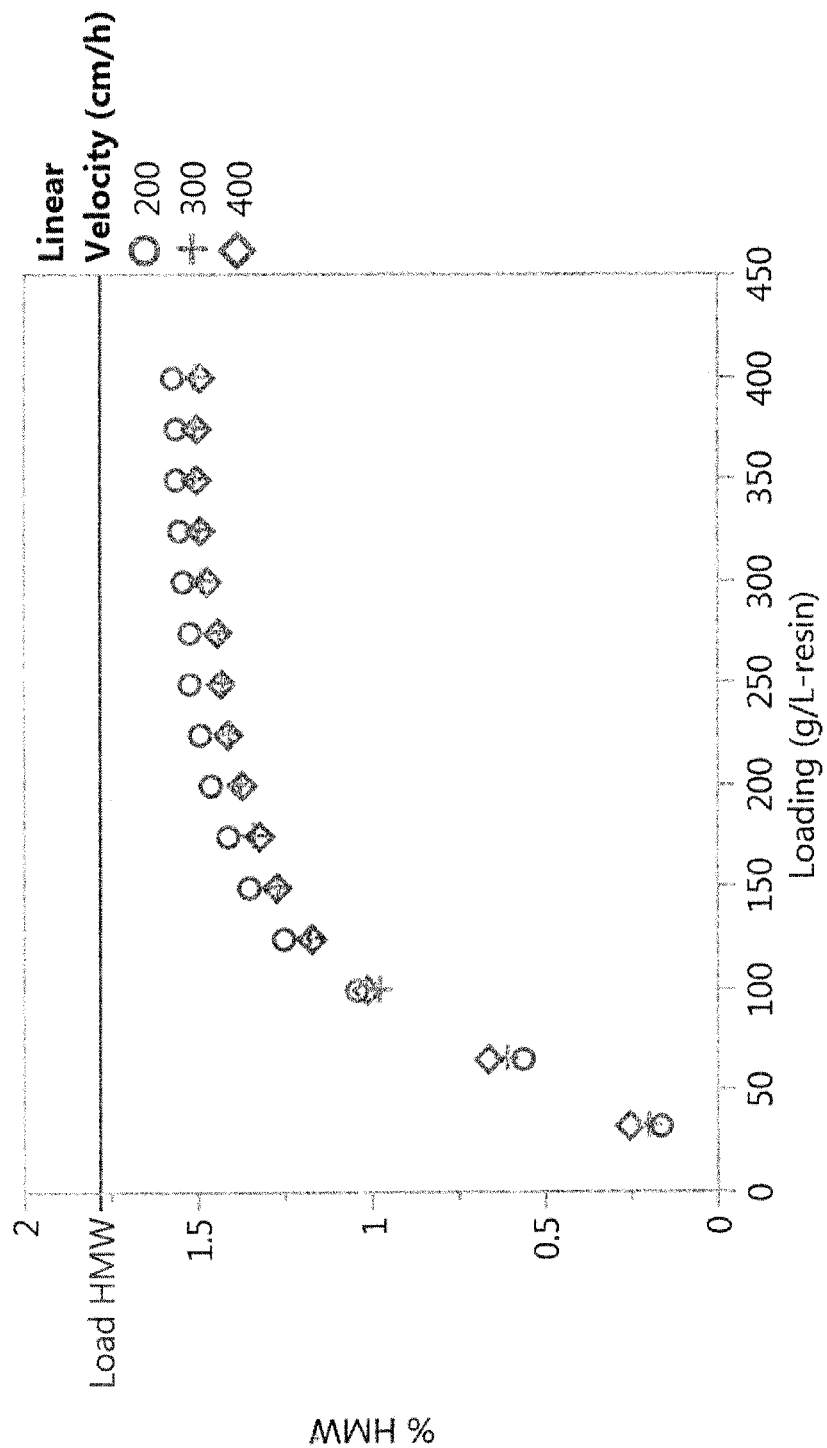
FIG. 7A is a plot of high molecular weight percentages as a function of loading, according to an aspect of the present disclosure.

High molecular weight percentages (HMW %) were plotted as a function of loading, as depicted in FIG. 7A. The HMW % of the load material was 1.78%. The cumulative pool HMW % at 200 g/L-resin and 400 g/L-resin are shown below in Table 3:

TABLE 3

| | 200 g/L-resin | 400 g/L-resin |
|---|---|---|
| 200 cm/hr | 1.10% | 1.34% |
| 300 cm/hr | 1.06% | 1.28% |
| 400 cm/hr | 1.07% | 1.28% |

Figure 7B:
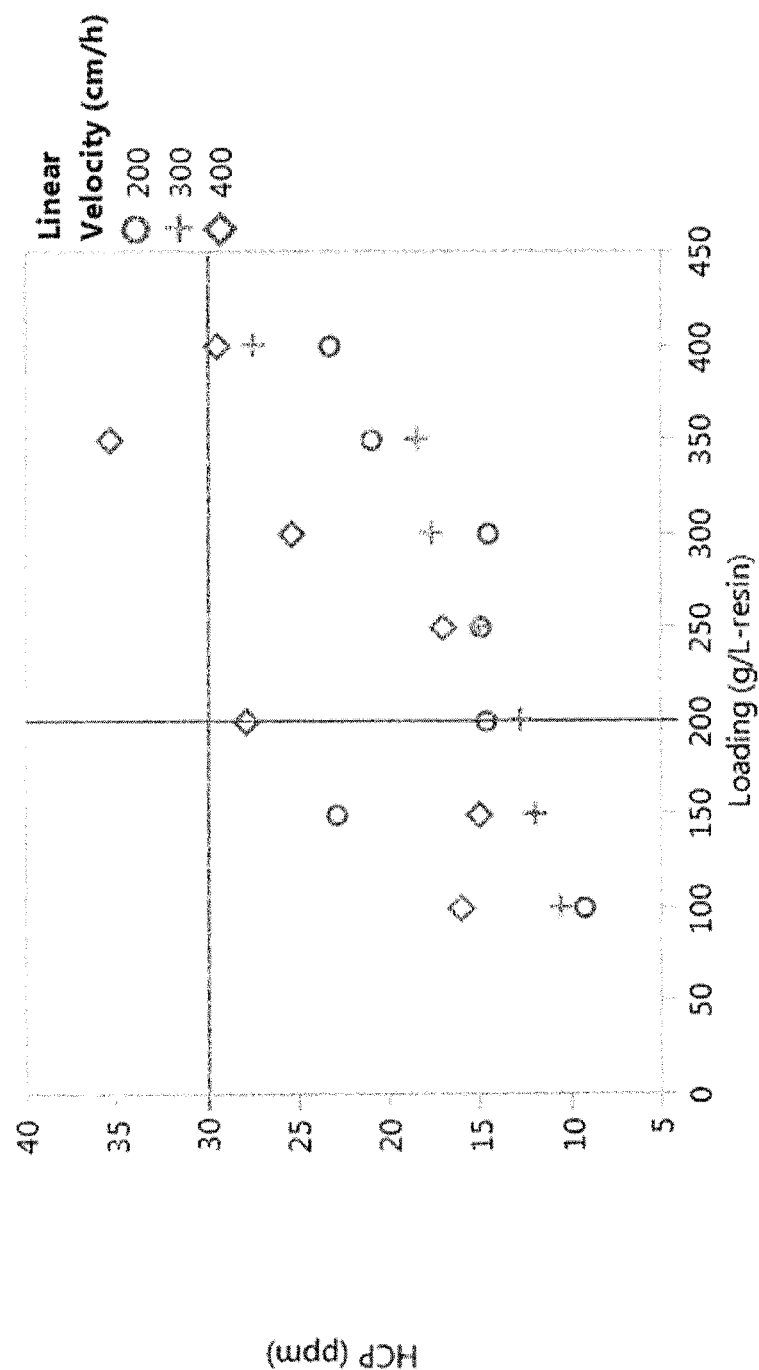
FIG. 7B is a plot of host cell protein quantity as a function of loading, according to an aspect of the present disclosure.

Host cell proteins were quantified in parts per million for each loading velocity using a F665 CHO HCP ELISA kit (Cygnus Technologies). The resulting quantities were plotted as a function of loading, as depicted in FIG. 7B. As a comparison, host cell proteins were quantified from an anion exchange chromatography pool of the same load material, and were found to be present at 549.61 ppm.

Example 5

Figure 7C:
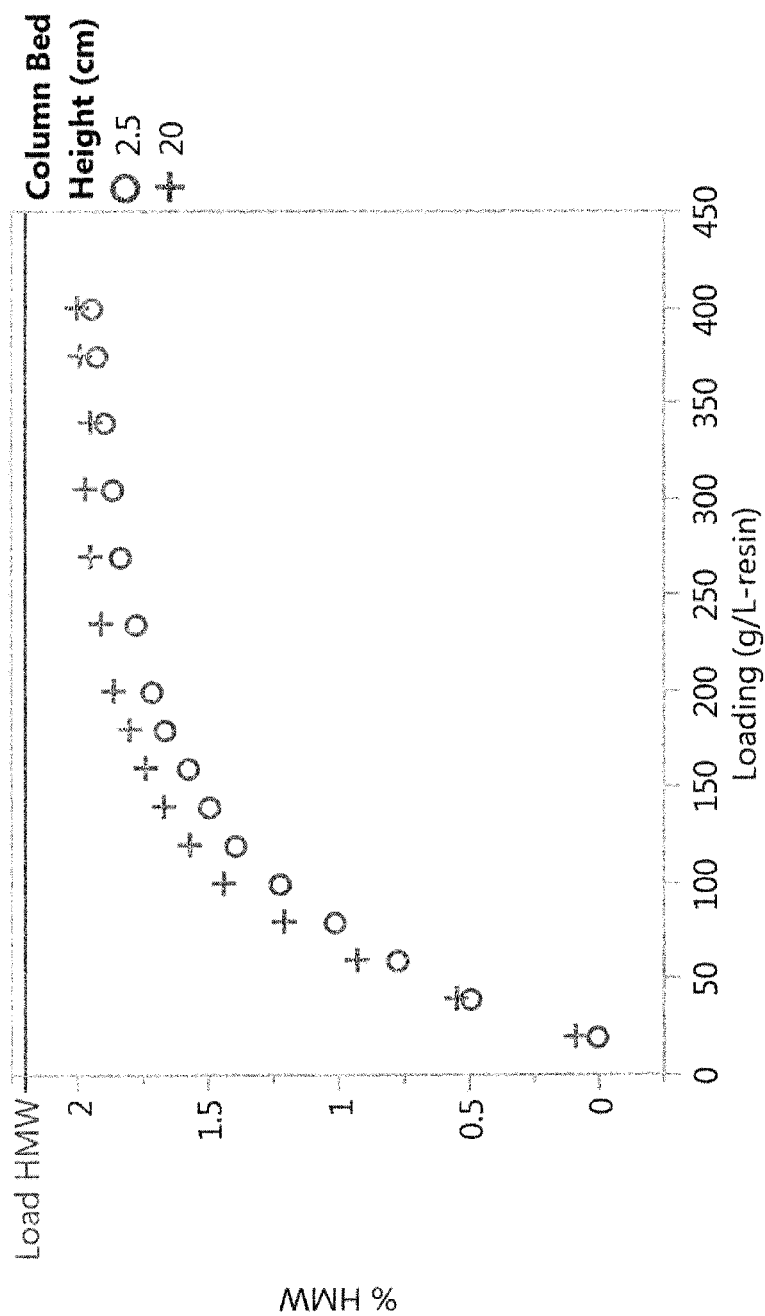
FIG. 7C is a plot of high molecular weight percentages as a function of loading concentration, according to an aspect of the present disclosure.

A target antibody was prepared using HIC in two columns having different bed heights (20 cm, as used in Example 4, and 2.5 cm). Both runs were performed such that the residence time in each column was 3 minutes (i.e., a 400 cm/hr linear velocity in the 20 cm bed height column). The HMW % for the load material was 2.2%. The HMW % for each column's pool was plotted as a function of loading concentration, as shown in FIG. 7C.

Example 6

An IgG1 target antibody was prepared using a HIC apparatus with three columns, configured to implement a continuous HIC protocol. Each HIC column in the HIC apparatus had a bed height of 10 cm and a 0.77 cm inner diameter. A continuous HIC protocol was implemented that repeated cyclically four times. The target antibody was loaded into columns undergoing a loading step of the protocol as a part of a mixture including 30 mM sodium citrate, balanced to a pH of 6.0. The target antibody was eluted from columns undergoing an elution step of the protocol with a buffer including 40 mM tris and 30 mM sodium citrate, balanced to a pH of 6.0±0.1. The columns were regenerated during a regeneration step of the protocol using a single-solution protocol with a single alkaline solution. The parameters and results of the protocol are summarized in Table 4, along with the parameters and results of Comparative Example B.

Comparative Example B

An IgG1 target polypeptide was prepared from a mixture using a conventional batch process, as a comparison to the methods of Example 6. The loading additives, wash buffer, stripping buffers, and equilibration buffers were identical to those used in the method of Example 6, but a conventional batch methodology was employed. As in Example 6, the target polypeptide was loaded as a part of a mixture including 30 mM sodium citrate, balanced to a pH of 6.0. The target polypeptide was eluted with a buffer including 40 mM tris and 30 mM sodium citrate, balanced to a pH of 6.0±0.1. A single-solution protocol with an alkaline solution was used during a regeneration step. The parameters and results are summarized in Table 4, along with the parameters and results of Example 6. As can be seen from the data in Table 4, the continuous HIC method of Example 6 was approximately 3.4 times as productive as the comparative batch process example.

TABLE 4

| Value | Example 6 | Comparative Example B |
|---|---|---|
| Volume of Hydrophobic Interaction Media used | 14.1 mL | 6.53 L |
| Loading rate | 4.7 mL/min | 1.05 L/min |
| Cycle Time | 0.75 hr | 2.48 hr |
| Load Concentration | 11.5 g/L | 10.8 g/L |
| Load Volume | 846 mL | 79.6 L |
| Load Mass | 97.3 g | 860 g |
| Load HMW % | 1.69% | 0.59% |
| Pool HMW % | 0.89% | 0.26% |
| Pool Concentration | 7.23 g/L | 7.92 g/L |
| Pool Volume | 1309 mL | 106.4 L |
| Pool Mass | 9.46 g | 843 g |
| HMW CF | 1.90 | 2.48 |
| Yield | 97.3% | 98.1% |
| Productivity | 179 g/L · hr | 52.1 g/L · hr |

Example 7

An IgG1 target polypeptide was prepared using a HIC apparatus with three columns, configured to implement a continuous HIC protocol. Each HIC column in the HIC apparatus had a bed height of 10 cm and a 0.77 cm inner diameter. A continuous HIC protocol was implemented that repeated cyclically four times. The target polypeptide was loaded into columns undergoing a loading step of the protocol as a part of a mixture including 30 mM sodium citrate, balanced to a pH of 5.5. The target polypeptide was eluted from columns undergoing an elution step of the protocol with a buffer including 40 mM tris and 30 mM sodium citrate, balanced to a pH of 5.5±0.1. The columns were regenerated during a regeneration step, using a single-solution protocol with a single alkaline solution. The parameters and results of the protocol are summarized in Table 5, along with the parameters and results of Comparative Example C.

Comparative Example C

An IgG1 target polypeptide was prepared from a mixture using a conventional batch process, as a comparison to the methods of Example 7. The loading additives, wash buffer, stripping buffers, and equilibration buffers were identical to those used in the method of Example 7, but a conventional batch methodology was employed. As in Example 7, the target polypeptide was loaded as a part of a mixture including 30 mM sodium citrate, balanced to a pH of 5.5. The target polypeptide was eluted with a buffer including 40 mM tris and 30 mM sodium citrate, balanced to a pH of 5.5±0.1. A single-solution protocol with an alkaline solution was used during a regeneration step. The results are summarized in Table 5, along with the parameters and results of Example 7. As can be seen from the data in Table 5, the continuous HIC method of Example 7 was approximately 2.1 times as productive as the comparative batch process example.

TABLE 5

| Value | Example 7 | Comparative Example C |
|---|---|---|
| Volume of Hydrophobic Interaction Media used | 14.1 mL | 6.53 L |
| Loading rate | 3.80 mL/min | 1.05 L/min |
| Cycle Time | 1.16 hr | 2.85 hr |
| Load Concentration | 11.9 g/L | 12.1 g/L |
| Load Volume | 803.7 mL | 104 L |
| Load Mass | 9.56 g | 1258 g |
| Load HMW % | 1.41% | 1.25% |
| Pool HMW % | 0.64% | 0.42% |
| Pool Concentration | 7.70 g/L | 9.45 g/L |
| Pool Volume | 1.1658 L | 58.5 L |
| Pool Mass | 2.90 g | 127.7 g |
| HMW CF | 2.2 | 3.0 |
| Yield | 93.9% | 95.9% |
| Productivity | 137.3 g/L · hr | 64.7 g/L · hr |

Example 8

An IgG4 target antibody was prepared using a HIC apparatus with four columns, configured to implement a continuous HIC protocol. Each HIC column in the HIC apparatus had a bed height of 2.5 cm and a 1.6 cm inner diameter. A continuous HIC protocol was implemented that repeated cyclically four times. The target antibody was loaded into columns undergoing a loading step of the protocol as a part of a mixture including 40 mM sodium citrate, balanced to a pH of 6.5. The target antibody was eluted from columns undergoing an elution step with a buffer including 40 mM tris and 40 mM sodium citrate, balanced to a pH of 6.5±0.1. The columns were regenerated during a regeneration step using a protocol that included a series of: (1) water, (2) an alkaline solution, (3) water, (4) an alcohol solution, and (5) water. The parameters and results are summarized in Table 6, along with the parameters and results of Comparative Example D.

Comparative Example D

A target polypeptide was prepared from a mixture using a conventional batch process, as a comparison to the methods of Example 7. The loading additives, wash buffer, stripping buffers, and equilibration buffers were identical to those used in the method of Example 8, but a conventional batch methodology was employed. As in Example 8, the target antibody was loaded as a part of a mixture including 40 mM sodium citrate, balanced to a pH of 6.5. The target antibody was eluted with a buffer including 40 mM tris and 40 mM sodium citrate, balanced to a pH of 6.5±0.1. The columns were regenerated using a protocol that included a series of: (1) water, (2) an alkaline solution, (3) water, (4) an alcohol solution, and (5) water. The parameters and results are summarized in Table 6, along with the parameters and results of Example 8. As can be seen from the data in Table 6, the continuous HIC method of Example 8 was approximately 5.7 times as productive as the comparative batch process example.

TABLE 6

| Value | Example 8 | Comparative Example D |
|---|---|---|
| Volume of Hydrophobic Interaction Media used | 20.0 mL | 3.18 L |
| Loading rate | 1.67 mL/min | 0.257 L/min |
| Cycle Time | 0.69 hr | 4.30 hr |
| Load Concentration | 11.6 g/L | 12.2 g/L |
| Load Volume | 300 mL | 45.0 L |
| Load Mass | 3.66 g | 590 g |
| Load HMW % | 1.01% | 0.90% |
| Pool HMW % | 0.45% | 0.25% |
| Pool Concentration | 6.45 g/L | 8.31 g/L |
| Pool Volume | 1.285 L | 34.7 L |
| Pool Mass | 8.29 g | 288 g |
| HMW CF | 2.2 | 3.6 |
| Yield | 86.4% | 89.4% |
| Productivity | 120.6 g/L · hr | 21.1 g/L · hr |

Example 9

Figure 8A:
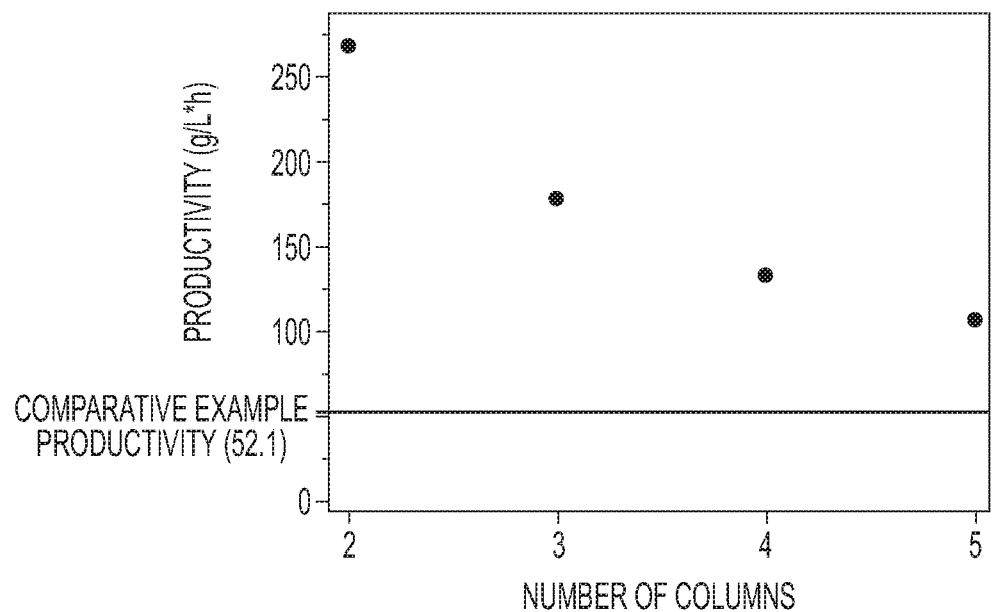
FIG. 8A is plot of productivity as a function of a number of chromatographic columns, according to an aspect of the present disclosure.

Data collected from Example 6 were used to develop a model describing the relationship between the number of columns a chromatography apparatus contains and the productivity of continuous HIC using the apparatus, where productivity was considered to be a measure of the grams of target antibody purified per liter of resin per hour (g/L*h). The model assumed the use of a single alkaline regeneration solution and an IgG1 target antibody. The model also assumed a constant 97.3% yield, a constant 4.7 mL/min load rate, a constant load concentration, and a constant 15 CV (column volume) load volume. When predicting a productivity for HIC apparatuses including more than three columns, theoretical wash, strip, and equilibration flow rates were adjusted to maintain a model having continuous occupancy of all the columns during continuous HIC. Further, for modeling the two-column apparatus in particular, it was assumed one column would be in a loading step and one column would be in a washing/stripping/regenerating step, omitting a two-stage loading step as in other continuous HIC protocols. Table 7 lists data used to generate the predicted productivity for each HIC apparatus. FIG. 8A shows a plot of the modeled relationship as compared to a batch productivity of 52.1 g/L·hr.

TABLE 7

| Number of Columns | 2 | 3 | 4 | 5 |
|---|---|---|---|---|
| Load/Looping Flow Rate | 4.7 | 4.7 | 4.7 | 4.7 |
| Wash/Strip/Equilibration Flow Rate | 4.7 | 4.7 | 2.5 | 1.9 |
| Cycle Time (minutes) | 30 | 45 | 60 | 75 |
| Cycle Time (hours) | 0.5 | 0.75 | 1 | 1.25 |
| Processing Time (hours) | 2.5 | 3.75 | 5 | 6.25 |
| Load Volume (CV) | 15 | 15 | 15 | 15 |
| Load Volume per Column (mL) | 70.5 | 70.5 | 70.5 | 70.5 |
| Load Protein per Column (mg) | 810.75 | 810.75 | 810.75 | 810.75 |
| Total Protein Loaded (g) | 6.486 | 9.729 | 12.972 | 16.215 |
| Total Protein Eluate (g) | 6.3109 | 9.4663 | 12.6218 | 15.7772 |
| Total Resin Volume (L) | 0.0094 | 0.0141 | 0.0188 | 0.0235 |
| Productivity (g/L*h) | 268.548 | 179.032 | 134.274 | 107.4192 |

Example 10

Figure 8B:
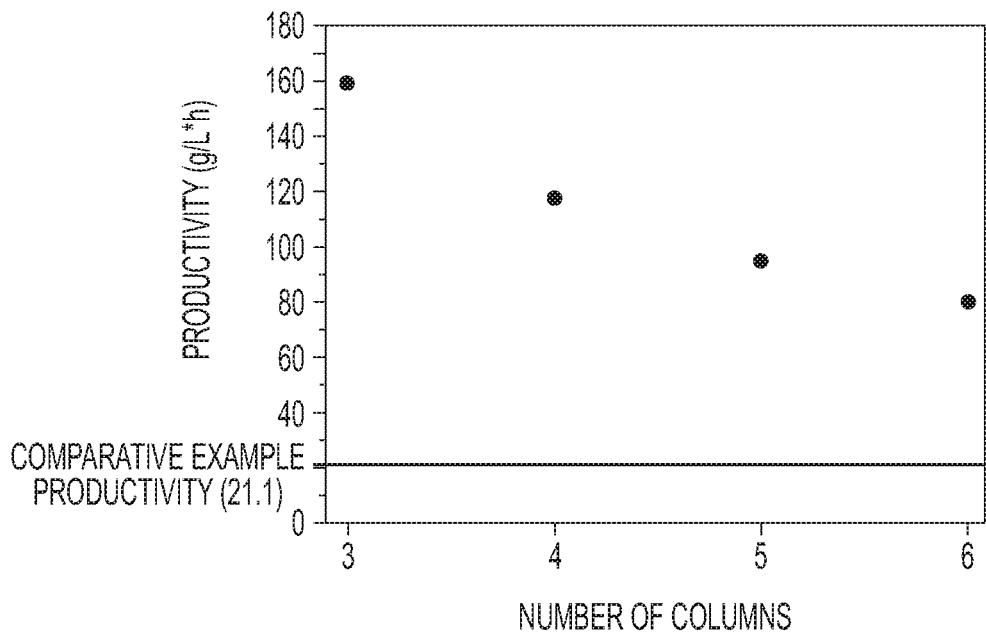
FIG. 8B is a plot of productivity as a function of a number of chromatographic columns, according to an aspect of the present disclosure.

Data collected from Example 8 were used to develop a model describing the relationship between the number of columns a chromatography apparatus contains and the productivity of continuous HIC using the apparatus. The model assumed the use of a multi-fluid regeneration procedure including water, an alkaline solution, and an alcohol solution. The model also assumed a constant 86.4% yield, a constant 5.0 mL/min load rate, a constant load concentration, and a constant 10.3 CV load volume. When predicting a productivity for HIC apparatuses including more than three columns, theoretical wash, strip, and equilibration flow rates were adjusted to maintain a model having continuous occupancy of all the columns during continuous HIC. Table 8 lists data used to generate the predicted productivity for each HIC apparatus. FIG. 8B shows a plot of the modeled relationship as compared to a batch productivity of 21.1 g/L·hr.

TABLE 8

| Number of Columns | 3 | 4 | 5 | 6 |
|---|---|---|---|---|
| Load/Looping Flow Rate | 5.0 | 5.0 | 5.0 | 5.0 |
| Wash/Strip/Equilibration Flow Rate | 7.8 | 3.9 | 2.6 | 1.9 |
| Cycle Time (minutes) | 31 | 42 | 52 | 62 |
| Cycle Time (hours) | 0.5167 | 0.7 | 0.8667 | 1.0333 |
| Processing Time (hours) | 2.5833 | 3.5 | 4.3333 | 5.1667 |
| Load Volume (CV) | 10.3 | 10.3 | 10.3 | 10.3 |
| Load Volume per Column (mL) | 51.6 | 51.6 | 51.6 | 51.6 |
| Load Protein per Column (mg) | 593.4 | 593.4 | 593.4 | 593.4 |
| Total Protein Loaded (g) | 7.1208 | 9.4944 | 11.868 | 14.2416 |
| Total Protein Eluate (g) | 6.1524 | 8.2032 | 10.2540 | 12.3047 |
| Total Resin Volume (L) | 0.015 | 0.02 | 0.025 | 0.03 |
| Productivity (g/L*h) | 158.7709 | 117.1880 | 94.6519 | 79.3854 |

Those skilled in the art will appreciate that the conception upon which this disclosure is based may readily be used as a basis for designing other methods and systems for carrying out the solutions and purposes of the present disclosure. Accordingly, the claims are not to be considered as limited by the foregoing description.

What is claimed is:

1. A method for preparing a target polypeptide from a mixture including the target polypeptide, the method comprising:
    passing the mixture including the target polypeptide to a first column of a plurality of chromatographic columns in a hydrophobic interaction chromatography (HIC) apparatus, wherein each of the plurality of columns comprises an outlet connectable to another column of the plurality of columns;
    passing an effluent including the target polypeptide from the first column to a second column of the plurality of columns;
    passing one or more mobile phases to a third column of the plurality of columns; and
    passing the target polypeptide through the outlets of each of the plurality of columns, wherein a sum of residence times for the mixture including the target polypeptide in the first column and second column is approximately the same as the sum of the residence times of the one or more mobile phases in the third column.

2. The method of claim 1, further comprising passing one or more mobile phases to each of the plurality of columns.

3. The method of claim 1, wherein passing one or more mobile phases to a column includes:
    passing a wash buffer to the column; and
    after passing a wash buffer to the column, regenerating the column, wherein regenerating the column comprises passing water, an alkaline solution, an alcohol solution, or an equilibration buffer to the column.

4. The method of claim 3, wherein the step of passing a target polypeptide through the outlet of a column occurs after a wash buffer has been passed to the column.

5. The method of claim 1, wherein one or more of an ultraviolet absorption, electrical conductivity, or pH of a resident solution are measured at the outlet of either the first column or second column.

6. The method of claim 3, wherein the HIC apparatus includes four columns and the sum of the residence times for the mixture including the target polypeptide in the first column and the second column is approximately the same as the sum of the regeneration times of the third column and the fourth columns.

7. The method of claim 1, wherein the target polypeptide is a monoclonal antibody.

8. The method of claim 1, wherein the one or more mobile phases comprises an equilibration buffer and a wash buffer.

9. The method of claim 1, wherein one or more of an ultraviolet absorption, electrical conductivity, or pH of a resident solution are measured at the outlets of each of the plurality of columns.

10. The method of claim 1, wherein the target polypeptide is prepared at a productivity greater than or equal to 50 g/L·hr.

11. The method of claim 10, wherein a percentage of high molecular weight species in the mixture is reduced by a BMW CF of at least approximately 1.3.

* * * * *

UNITED STATES PATENT AND TRADEMARK OFFICE
CERTIFICATE OF CORRECTION

PATENT NO. : 11,884,698 B2
APPLICATION NO. : 16/459187
DATED : January 30, 2024
INVENTOR(S) : Isabelle Livigni et al.

It is certified that error appears in the above-identified patent and that said Letters Patent is hereby corrected as shown below:

On the Title Page

In the References Cited, under the Other Publications, in Column 2, Line 1, Delete ""Wolk et al. Improving" and insert -- "Wolk et al. "Improving --.

In the Claims

In Claim 11, Column 30, Line 62, delete "BMW" and insert -- HMW --.

Signed and Sealed this
Twelfth Day of March, 2024

*Katherine Kelly Vidal*

Katherine Kelly Vidal
*Director of the United States Patent and Trademark Office*